(12) United States Patent
Griffis, III et al.

(10) Patent No.: US 9,592,152 B2
(45) Date of Patent: Mar. 14, 2017

(54) APPARATUS AND METHOD FOR SECURING OCULAR TISSUE

(75) Inventors: Jack C. Griffis, III, Decatur, GA (US); David G. Ozinga, Flower Mound, TX (US)

(73) Assignee: Refocus Group, Inc., Dallas, TX (US)

( * ) Notice: Subject to any disclaimer, the term of this patent is extended or adjusted under 35 U.S.C. 154(b) by 0 days.

(21) Appl. No.: 13/413,218

(22) Filed: Mar. 6, 2012

(65) Prior Publication Data

US 2012/0226107 A1 Sep. 6, 2012

Related U.S. Application Data

(63) Continuation-in-part of application No. 11/827,444, filed on Jul. 11, 2007, now Pat. No. 8,709,029.

(60) Provisional application No. 60/819,995, filed on Jul. 11, 2006.

(51) Int. Cl.
| | | |
|---|---|---|
| A61B 1/32 | (2006.01) | |
| A61F 9/007 | (2006.01) | |
| A61F 2/14 | (2006.01) | |
| A61B 17/30 | (2006.01) | |
| A61F 9/013 | (2006.01) | |

(52) U.S. Cl.
CPC .............. *A61F 9/007* (2013.01); *A61F 2/14* (2013.01); *A61B 2017/306* (2013.01); *A61F 9/013* (2013.01)

(58) Field of Classification Search
CPC .......... A61B 2017/30; A61B 2017/303; A61B 2017/306; A61F 2/147; A61F 2/148; A61F 9/0136

USPC ........................ 600/236; 606/166; 351/217
See application file for complete search history.

(56) References Cited

U.S. PATENT DOCUMENTS

| | | | | |
|---|---|---|---|---|
| 4,124,905 | A | * 11/1978 | Clark | .................... A61F 2/1662 606/107 |
| 4,205,682 | A | 6/1980 | Crock et al. | |
| 4,275,733 | A | 6/1981 | Marinoff | |
| 4,340,059 | A | 7/1982 | Marinoff | |
| 4,688,570 | A | * 8/1987 | Kramer et al. | ................ 606/166 |
| 4,865,033 | A | 9/1989 | Krumeich et al. | |
| 5,002,569 | A | * 3/1991 | Lindstrom | ............ A61F 2/1613 623/6.15 |
| 5,009,660 | A | 4/1991 | Clapham | |
| 5,092,863 | A | * 3/1992 | Schanzlin | ......................... 606/5 |
| 5,098,443 | A | 3/1992 | Parel et al. | |

(Continued)

FOREIGN PATENT DOCUMENTS

| | | |
|---|---|---|
| CN | 1043257 A | 6/1990 |
| EP | 0 336 065 A2 | 10/1989 |

(Continued)

OTHER PUBLICATIONS

Office Action dated Nov. 8, 2012 in connection with U.S. Appl. No. 11/827,444.

(Continued)

*Primary Examiner* — Gregory Anderson
*Assistant Examiner* — Sarah Simpson

(57) ABSTRACT

An ocular fixation device includes a body configured to be placed on an eye. The ocular fixation device also includes multiple twist picks configured to be turned to secure the body to the eye and to release the body from the eye. The body includes connection points on which a surgical tool is mountable on the body.

26 Claims, 20 Drawing Sheets

(56) References Cited

U.S. PATENT DOCUMENTS

| | | | |
|---|---|---|---|
| 5,437,658 A * | 8/1995 | Muller et al. | 606/5 |
| 5,489,299 A | 2/1996 | Schachar | |
| 6,342,053 B1 | 1/2002 | Berry | |
| 6,527,780 B1 | 3/2003 | Wallace et al. | |
| 6,623,476 B2 * | 9/2003 | Juhasz et al. | 606/5 |
| 6,863,667 B2 | 3/2005 | Webb et al. | |
| 7,087,050 B2 | 8/2006 | LaHaye | |
| 7,189,225 B2 | 3/2007 | Rosen | |
| 7,189,248 B2 | 3/2007 | Schachar et al. | |
| 2002/0103481 A1 | 8/2002 | Webb et al. | |
| 2002/0120285 A1 | 8/2002 | Schachar et al. | |
| 2004/0054374 A1 | 3/2004 | Weber et al. | |
| 2004/0073231 A1 * | 4/2004 | Juan, Jr. | A61F 9/00727 606/108 |
| 2004/0073245 A1 | 4/2004 | Schachar et al. | |
| 2004/0267294 A1 * | 12/2004 | Will | 606/166 |
| 2006/0129129 A1 | 6/2006 | Smith | |
| 2006/0241750 A1 | 10/2006 | Zdenek et al. | |
| 2006/0271025 A1 | 11/2006 | Jones et al. | |
| 2007/0162115 A1 * | 7/2007 | Hermeking | A61F 2/1694 623/4.1 |

FOREIGN PATENT DOCUMENTS

| | | |
|---|---|---|
| EP | 1033120 A2 | 9/2000 |
| EP | 1 099 432 A2 | 5/2001 |
| GB | 1456746 | 11/1976 |
| JP | 2000175954 A | 6/2000 |
| JP | 2000279441 A | 10/2000 |
| JP | 2001187081 A | 7/2001 |
| JP | 2002143209 A | 5/2002 |
| JP | 2003339756 A | 12/2003 |
| JP | 2004531344 A | 10/2004 |
| JP | 2006006605 A | 1/2006 |
| WO | WO 91/14406 A1 | 10/1991 |
| WO | WO 94/07424 A1 | 4/1994 |
| WO | WO 95/15120 A1 | 6/1995 |
| WO | WO 95/28984 A1 | 11/1995 |
| WO | WO 00/21466 A1 | 4/2000 |
| WO | WO 00/74600 A1 | 12/2000 |
| WO | WO 2006/014484 A2 | 2/2006 |

OTHER PUBLICATIONS

Notification of Transmittal of the International Search Report and the Written Opinion of the International Searching Authority, or the Declaration dated Nov. 7, 2008 in PCT Application No. PCT/US2007/015774.

"Instruments to help with those frustration situations", Surgical Solutions from Katena, 4 pages.

Communication pursuant to Article 94(3) EPC dated Aug. 2, 2011 in connection with European Patent Application No. EP 07 836 052.6.

Annex to Form PCT/ISA/206 Communication Relating to the Results of the Partial International Search dated Apr. 10, 2008 in PCT Application No. PCT/US2007/015774.

Notification of Transmittal of the International Search Report and the Written Opinion of the International Searching Authority, or the Declaration dated Mar. 18, 2009 in connection with PCT Application No. PCT/US2007/015816.

Japanese Office Action in connection with Japanese Patent Application No. 2009-519513, May 15, 2012, 10 pages.

Extended European Search Report in connection with European Patent Application No. 12172628.5, Oct. 19, 2012, 8 pages.

First Office Action dated Aug. 21, 2015 in connection with Canadian Patent Application No. 2,853,984; 4 pages.

* cited by examiner

1. ENGAGE

2. DOCK

BLADE READY

BLADE PASSED THRU

APPARATUS AND METHOD FOR SECURING OCULAR TISSUE

CROSS-REFERENCE TO RELATED PATENT DOCUMENTS

This application claims priority under 35 U.S.C. §120 as a continuation-in-part of U.S. patent application Ser. No. 11/827,444, filed Jul. 11, 2007, now U.S. Pat. No. 8,709,029 which claims priority under 35 U.S.C. §119(e) to U.S. Provisional Patent Application No. 60/819,995 filed on Jul. 11, 2006. Both of these applications are hereby incorporated by reference.

This application is related to the following U.S. patent applications and issued patents:
  (1) U.S. Pat. No. 6,007,578 entitled "Scleral Prosthesis for Treatment of Presbyopia and Other Eye Disorders" issued on Dec. 28, 1999;
  (2) U.S. Pat. No. 6,280,468 entitled "Scleral Prosthesis for Treatment of Presbyopia and Other Eye Disorders" issued on Aug. 28, 2001;
  (3) U.S. Pat. No. 6,299,640 entitled "Scleral Prosthesis for Treatment of Presbyopia and Other Eye Disorders" issued on Oct. 9, 2001;
  (4) U.S. Pat. No. 5,354,331 entitled "Treatment of Presbyopia and Other Eye Disorders" issued on Oct. 11, 1994;
  (5) U.S. Pat. No. 5,465,737 entitled "Treatment of Presbyopia and Other Eye Disorders" issued on Nov. 14, 1995;
  (6) U.S. Pat. No. 5,489,299 entitled "Treatment of Presbyopia and Other Eye Disorders" issued on Feb. 6, 1996;
  (7) U.S. Pat. No. 5,503,165 entitled "Treatment of Presbyopia and Other Eye Disorders" issued on Apr. 2, 1996;
  (8) U.S. Pat. No. 5,529,076 entitled "Treatment of Presbyopia and Other Eye Disorders" issued on Jun. 25, 1996;
  (9) U.S. Pat. No. 5,722,952 entitled "Treatment of Presbyopia and Other Eye Disorders" issued on Mar. 3, 1998;
  (10) U.S. Pat. No. 6,197,056 entitled "Segmented Scleral Band for Treatment of Presbyopia and Other Eye Disorders" issued on Mar. 6, 2001;
  (11) U.S. Pat. No. 6,579,316 entitled "Segmented Scleral Band for Treatment of Presbyopia and Other Eye Disorders" issued on Jun. 17, 2003;
  (12) U.S. Pat. No. 6,926,727 entitled "Surgical Blade for Use with a Surgical Tool for Making Incisions for Scleral Eye Implants" issued on Aug. 9, 2005;
  (13) U.S. Pat. No. 6,991,650 entitled "Scleral Expansion Device Having Duck Bill" issued on Jan. 31, 2006;
  (14) U.S. patent application Ser. No. 10/080,877 entitled "System and Method for Making Incisions for Scleral Eye Implants" filed on Feb. 22, 2002;
  (15) U.S. patent application Ser. No. 10/443,122 entitled "System and Method for Determining a Position for a Scleral Pocket for a Scleral Prosthesis" filed on May 20, 2003;
  (16) U.S. patent application Ser. No. 11/137,085 entitled "Scleral Prosthesis for Treatment of Presbyopia and Other Eye Disorders" filed on May 24, 2005;
  (17) U.S. patent application Ser. No. 11/199,591 entitled "Surgical Blade for Use with a Surgical Tool for Making Incisions for Scleral Eye Implants" filed on Aug. 8, 2005;
  (18) U.S. patent application Ser. No. 11/252,369 entitled "Scleral Expansion Device Having Duck Bill" filed on Oct. 17, 2005;
  (19) U.S. patent application Ser. No. 11/323,283 entitled "Surgical Blade for Use with a Surgical Tool for Making Incisions for Scleral Eye Implants" filed on Dec. 30, 2005;
  (20) U.S. patent application Ser. No. 11/323,284 entitled "System and Method for Making Incisions for Scleral Eye Implants" filed on Dec. 30, 2005;
  (21) U.S. patent application Ser. No. 11/322,728 entitled "Segmented Scleral Band for Treatment of Presbyopia and Other Eye Disorders" filed on Dec. 30, 2005; and
  (22) U.S. patent application Ser. No. 11/323,752 entitled "Segmented Scleral Band for Treatment of Presbyopia and Other Eye Disorders" filed on Dec. 30, 2005.

All of these U.S. patents and patent applications are hereby incorporated by reference.

TECHNICAL FIELD

This disclosure is generally directed to surgical devices and more specifically to an apparatus and method for securing ocular tissue.

BACKGROUND

It is often desirable or necessary to secure a patient's eye in place during ocular surgery. For example, it is possible to restore the accommodative power to a presbyopic eye by implanting scleral prostheses within the sclera of the patient's eye. It is also possible to treat glaucoma, ocular hypertension, elevated intraocular pressure, or other eye disorders by implanting scleral prostheses within the sclera of the patient's eye. During these types of procedures, an incision can be made in the sclera of the eye and extended under the surface of the sclera to form a scleral "tunnel." A scleral prosthesis can then be placed within the tunnel. Before performing a surgical procedure to implant scleral prostheses or other surgical eye procedure, the patient's eye often needs to be fixated so that the patient's eye does not move during the surgical procedure.

FIGS. 18A and 18B illustrate a conventional ocular fixation tool. This ocular fixation tool is placed on the surface of a patient's eye and is physically sutured to the sclera of the patient's eye. This ocular fixation tool includes various notches in which a surgical tool can be placed.

FIG. 19 illustrates a second conventional ocular fixation tool having a solid ring with spikes (not shown) that can be depressed into the tissue of a patient's eye. This ocular fixation tool also includes a handle rotatably coupled to the solid ring, where the handle can be used to move and position the tool. In addition, this ocular fixation tool includes a projection from the solid ring, where a surgical tool can be mounted on the projection.

FIGS. 20A and 20B illustrate a third conventional ocular fixation tool having a handle, a solid ring, and two rotatable arms. The solid ring is rotatably coupled to the handle. The two rotatable arms are coupled to or mounted on the solid ring at a common pivot point. As shown in FIG. 20A, the two rotatable arms are in the open position, and the solid ring may be placed in a desired location on a patient's eye. As shown in FIG. 20B, the two rotatable arms can then be closed, which drives prongs or other extensions on the arms into the tissue of the patient's eye. After that, the handle can be rotated sideways so that a surgeon or tool has clear access to the patient's eye through the rings. In other embodiments, the handle and the solid ring can be omitted, and the two rotatable arms could be used by themselves (the arms can be closed and opened to lock onto and release a patient's ocular tissue). In still other embodiments, the two rotatable arms could lack prongs or other extensions themselves, and the arms could be used to drive pins or other extensions on the solid ring into a patient's ocular tissue.

SUMMARY

This disclosure provides an apparatus and method for securing ocular tissue.

In a first embodiment, an ocular fixation device includes a body configured to be placed on an eye. The ocular fixation device also includes multiple twist picks configured to be turned to secure the body to the eye and to release the body from the eye. The body includes connection points on which a surgical tool is mountable on the body.

In a second embodiment, a system includes a surgical tool and an ocular fixation device. The ocular fixation device includes a body configured to be placed on the eye and multiple twist picks configured to be turned to secure the body to the eye and to release the body from the eye. The body includes connection points on which the surgical tool is mountable on the body.

In a third embodiment, an ocular fixation device includes a body configured to be placed on an eye. The body includes multiple openings configured to receive multiple twist picks that secure the body to the eye and release the body from the eye. The body also includes connection points on which a surgical tool is mountable on the body.

Other technical features may be readily apparent to one skilled in the art from the following figures, descriptions, and claims.

BRIEF DESCRIPTION OF THE DRAWINGS

For a more complete understanding of this disclosure, reference is now made to the following description, taken in conjunction with the accompanying drawing, in which.

DETAILED DESCRIPTION

FIGS. 1A through 1F illustrate a first example ocular fixation device 100 in accordance with this disclosure. The embodiment of the ocular fixation device 100 shown in FIGS. 1A through 1F is for illustration only. Other embodiments of the ocular fixation device 100 could be used without departing from the scope of this disclosure.

Figure 1A:
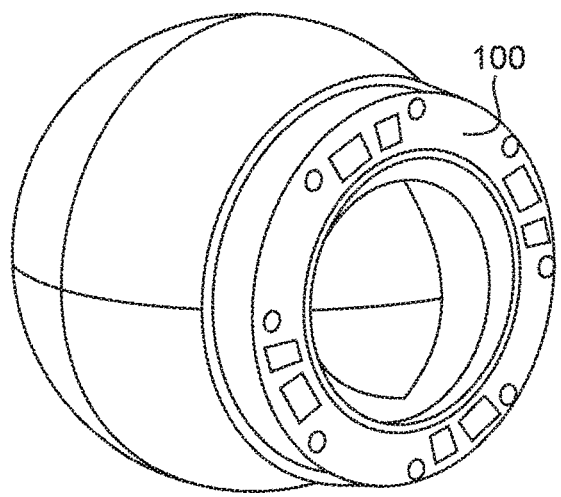
FIGS. 1A through 1F illustrate a first example ocular fixation device in accordance with this disclosure.
Figure 1B:
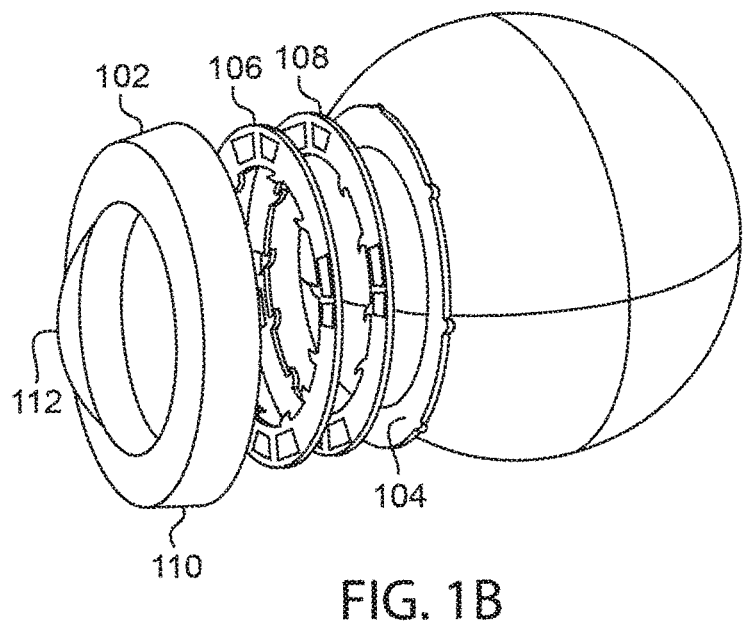

As shown in FIGS. 1A and 1B, the ocular fixation device 100 includes a body portion 102, a retention ring 104, and two locking rings 106-108. In this example, the body portion 102 includes a base 110 and a dome 112. The base 110 in this embodiment is generally circular and is used to house the retention ring 104 and the locking rings 106-108. The dome 112 represents a protective cover or shield that can be used to protect the central portion of a patient's eye. The body portion 102 could be formed from any suitable material(s), such as one or more transparent or opaque materials. The body portion 102 could also be formed using any suitable technique, such as injection molding.

The locking rings 106-108 can be inserted into the body portion 102 and the retention ring 104 can be attached to the body portion 102, which secures the locking rings 106-108 within the body portion 102. The retention ring 104 could be formed from any suitable material(s). The retention ring 104 could also be formed in any suitable manner, such as by injection molding.

Figure 1C:
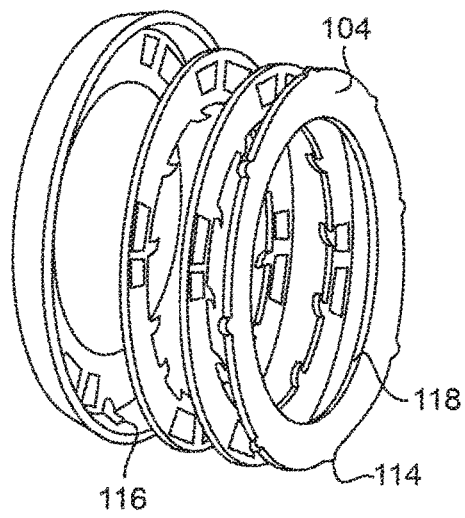

The retention ring 104 could be attached or secured to the body portion 102 in any suitable manner. For example, as shown in FIG. 1C, the retention ring 104 could include bumps 114, and the body portion 102 could include corresponding receptacles 116. In this embodiment, the retention ring 104 could be pushed into the body portion 102 until the bumps 114 engage the receptacles 116, locking the retention ring 104 in place.

As shown in FIG. 1C, the retention ring 104 could also have a slanted or tapered inner edge 118. This may help to facilitate placement of the ocular fixation tool 100 on a patient's eye. For example, the edge 118 of the retention ring 104 may be slanted so that it is substantially parallel to the portion of the patient's sclera on which the retention ring 104 rests.

Figure 1D:
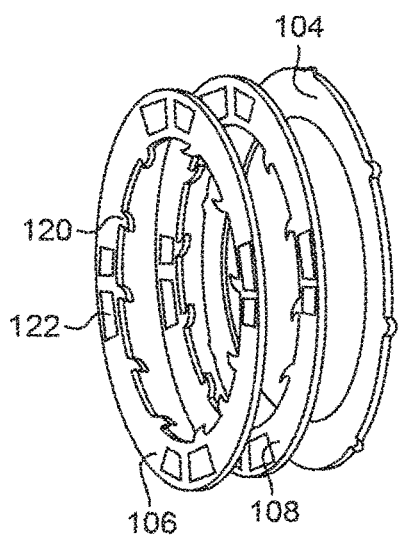
Figure 1E:
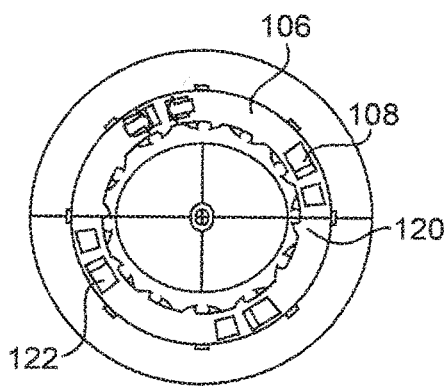

The locking rings 106-108 are used to secure the ocular fixation device 100 to a patient's eye, thereby helping to fixate and prevent movement of the patient's eye. As shown in FIGS. 1D and 1E, the locking rings 106-108 may include teeth 120. In this example, the locking rings 106-108, including the teeth 120, are substantially planar (although angled teeth could be used). Also, the teeth 120 in different locking rings 106-108 are angled towards each other. At least one of the locking rings 106-108 can rotate with respect to the other locking ring. In this way, the areas between the teeth 120 of the locking rings 106-108 can be increased and decreased. This allows the teeth 120 to grasp ocular tissue when the teeth 120 are pushed closer together. This also allows the teeth 120 to release the ocular tissue when the teeth 120 are pushed farther apart. In some embodiments, the locking rings 106-108 can be sized so that the teeth 120 attach or lock onto scleral tissue of a patient's eye (beyond the cornea and other areas in the central portion of the patient's eye). The locking rings 106-108 could be formed from any suitable material(s), such as a metal. The locking rings 106-108 could also be formed in any suitable manner, such as by photo-etching.

Figure 1F:
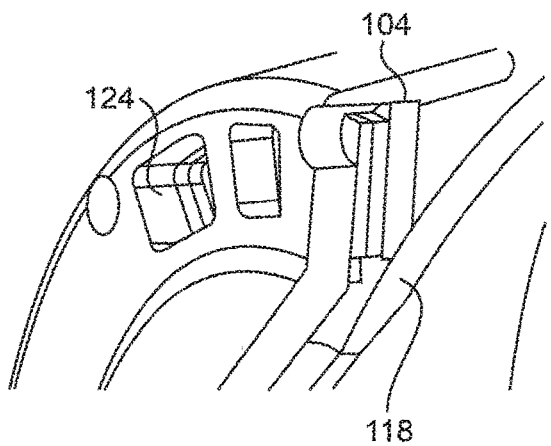

As shown in FIGS. 1D through 1F, the locking rings 106-108 include windows 122, and the body portion 102 includes corresponding windows 124. In some embodiments, a surgeon could insert a tool through one of the windows 124 and use the tool to cause one or more of the locking rings 106-108 to move. For example, the surgeon could insert a tool through one of the windows 124 and push or pull one of the locking rings 106-108, causing the openings between the teeth 120 of the locking rings 106-108 to open or close. As another example, the surgeon could insert a tool through one of the windows 124 and push both locking rings 106-108 together, causing the openings between the teeth 120 of the locking rings 106-108 to close. In other embodiments, part or all of the body portion 102 could be designed to rotate, causing the locking ring 106 to rotate with respect to the locking ring 108. This may allow, for example, the ocular fixation device 100 to be placed on a patient's eye and then rotated to lock the ocular fixation device 100 onto the patient's eye. Any other or additional technique could be used to cause the teeth 120 of the locking rings 106-108 to move with respect to each other.

Figure 2A:
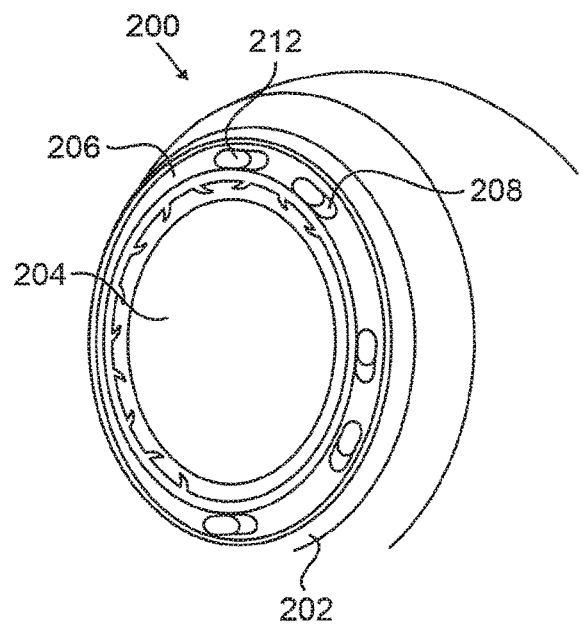
FIGS. 2A through 2C illustrate a second example ocular fixation device in accordance with this disclosure.
Figure 2B:
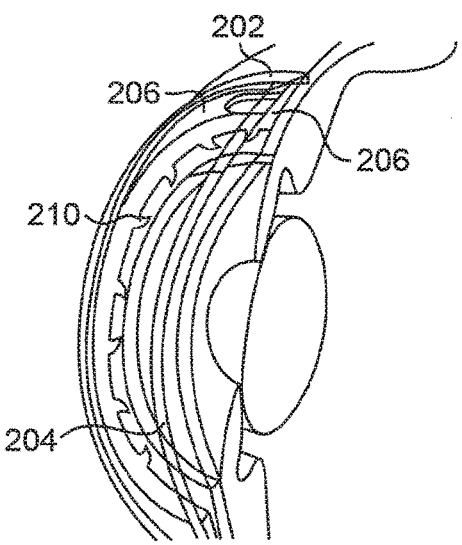
Figure 2C:
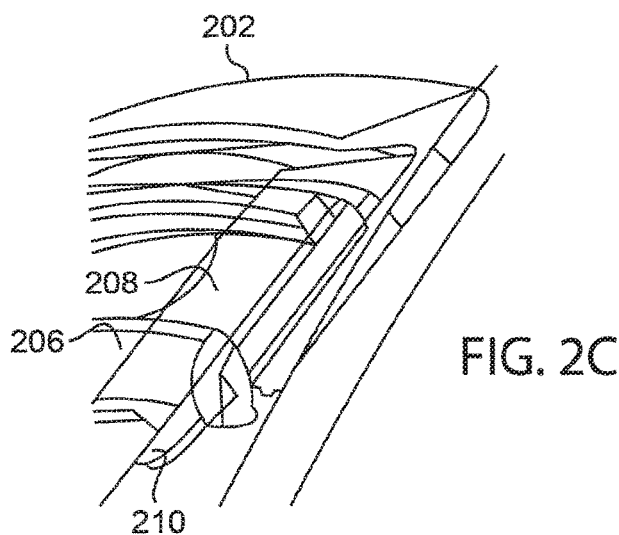

FIGS. 2A through 2C illustrate a second example ocular fixation device 200 in accordance with this disclosure. The embodiment of the ocular fixation device 200 shown in FIGS. 2A through 2C is for illustration only. Other embodiments of the ocular fixation device 200 could be used without departing from the scope of this disclosure.

The ocular fixation device 200 of FIGS. 2A through 2C operates in a similar manner as the ocular fixation device 100 of FIGS. 1A through 1F. As shown in FIG. 2A, the ocular fixation device 200 includes a base 202, a dome 204, and locking rings 206-208. Cross-sections showing additional structural details of the ocular fixation device 200 are shown in FIGS. 2B and 2C. As shown here, the base 202 is attached or secured to the dome 204 (or vice versa), helping to retain the locking rings 206-208 that are located between the base 202 and the dome 204. In this example, the cross-section of the base 202 includes a generally flat portion on which the locking rings 206-208 lie. The cross-section of the base 202 also includes a projection along its outer edge, which is attached to or helps secure the dome 204. The base 202 could further have a shape that facilitates its placement on a patient's eye, such as where the flat portion of the base 202 is slanted or sloped to approximately match a curvature of the patient's sclera. The base 202 could be formed from any suitable material(s). The base 202 could also be formed using any suitable technique, such as injection molding.

The dome 204 represents a protective cover or shield protecting the central portion of a patient's eye. The dome 204 could be formed from any suitable material(s), such as one or more transparent or opaque materials. The dome 204 could also be formed using any suitable technique, such as injection molding.

The locking rings 206-208 are located between the base 202 and the dome 204. In this example, the locking rings 206-208 include teeth 210 for attaching or locking onto ocular tissue of a patient's eye. At least one of the locking rings 206-208 can rotate with respect to the other locking ring to open and close the areas between the teeth 210 of the locking rings 206-208. This allows the teeth 210 to attach to and release ocular tissue of the patient's eye. In some embodiments, the locking rings 206-208 can be sized so that the teeth 210 attach to scleral tissue of a patient's eye. The locking rings 206-208 could be formed from any suitable material(s), such as a metal. The locking rings 206-208 could also be formed in any suitable manner, such as by photo-etching.

In this example, the locking rings 206-208 are not completely planar. Instead, each of the locking rings 206-208 includes a main section that is relatively planar and a curved section along its inner edge. The curved section of the locking ring 206 generally lies over and to the inside of the curved section of the locking ring 208. Also, the curved sections of the locking rings 206-208 include, are attached to, or carry the teeth 210 of the locking rings 206-208. In addition, the teeth 210 could be planar or angled with respect to the flat portions of the locking rings 206-208.

As shown here, each of the locking rings 206-208 includes one or more windows 212. The windows 212 can be used to identify the amount of space between the teeth 210 of the locking rings 206-208. For example, when the windows 212 of the locking rings 206-208 are aligned or nearly aligned, this may indicate that the areas between the teeth 210 of the locking rings 206-208 are substantially closed (the teeth 210 are attached or locked onto the ocular tissue of a patient's eye). Similarly, when the windows 212 of the locking rings 206-208 are not aligned very much, this may indicate that the areas between the teeth 210 of the locking rings 206-208 are substantially open (the ocular tissue of a patient's eye is not locked or has been released).

In the illustrated example, the dome 204 may cover the windows 212 of the locking rings 206-208, which could prevent the use of external tools to move the locking rings 206-208. To facilitate the attachment and release of ocular tissue by the ocular fixation device 200, one or both of the locking rings 206-208 could be rotated, such as via rotation of the dome 204 or the base 202. For example, the locking ring 206 could be fixed with respect to the dome 204, and/or the locking ring 208 could be fixed with respect to the base 202. The ocular fixation device 200 could be placed on a patient's eye, and a surgeon could rotate the dome 204 of the ocular fixation device 200. This may cause one of the locking rings 206-208 to rotate with respect to the other locking ring, thereby opening and closing the areas between the teeth 210 of the locking rings 206-208. This technique is for illustration only, and any other suitable technique could be used to attach and release ocular tissue using the ocular fixation device 200. For instance, windows could be formed in the dome 204 above the windows 212 in the locking rings 206-208, allowing the use of an external tool by the surgeon.

Figure 3A:
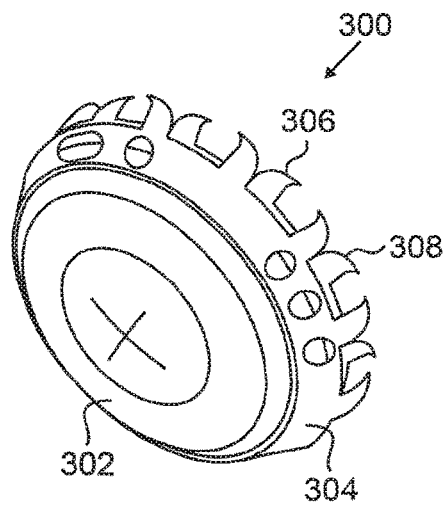
FIGS. 3A through 3C illustrate a third example ocular fixation device in accordance with this disclosure.
Figure 3B:
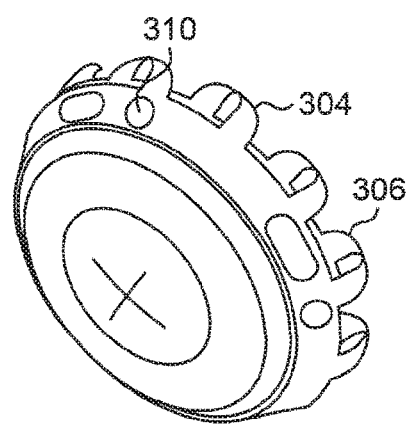
Figure 3C:
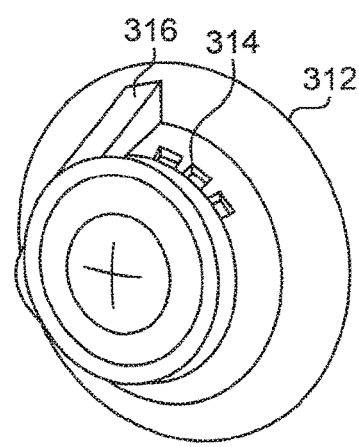

FIGS. 3A through 3C illustrate a third example ocular fixation device 300 in accordance with this disclosure. The embodiment of the ocular fixation device 300 shown in FIGS. 3A through 3C is for illustration only. Other embodiments of the ocular fixation device 300 could be used without departing from the scope of this disclosure.

As shown in FIG. 3A, the ocular fixation device 300 includes a dome 302 and locking rings 304-306. Once again, the dome 302 protects the central portion of a patient's eye and can be formed from any suitable material(s) and in any suitable manner. In this example, the dome 302 is transparent and includes a mark used to center the dome 302 on the patient's eye, although other embodiments could be used. Also, the locking rings 304-306 include teeth 308 that are shaped and positioned so that they are angled towards each other. This allows the teeth 308 of the locking rings 304-306 to attach or lock onto the ocular tissue (such as the scleral tissue) of a patient's eye. As shown in FIGS. 3A and 3B, at least one of the locking rings 304-306 is rotatable with respect to the other to open and close the areas between the teeth 308.

In this example, the locking rings 304-306 include windows 310, which can provide an indication of whether (and to what extent) the locking rings 304-306 are locked onto ocular tissue. For example, when the locking rings 304-306 are opened (not attached to ocular tissue), the windows 310 in the locking rings 304-306 may be at least partially aligned. When the locking rings 304-306 are closed (locked onto ocular tissue), the windows 310 in the locking rings 304-306 are not aligned, and the windows 310 in the locking ring 306 might be hidden.

As shown in FIG. 3C, the ocular fixation device 300 can further include a housing 312. The housing 312 holds the locking rings 304-306 and the dome 302 of the ocular fixation device 300. The housing 312 may also allow a surgeon to rotate at least one of the locking rings 304-306. In this example, the housing 312 includes windows 314 and connection points 316. The windows 314 in the housing 312 may be aligned with the windows 310 in the locking ring 304. This allows the surgeon to determine to what extent the locking rings 304-306 are opened or closed (since the housing 312 otherwise hides or covers the locking rings 304-306). The connection points 316 represent areas where a surgical tool can be attached to the housing 312 (described in more detail below), although the connection points 316 can be omitted if desired. The housing 312 can be formed from any suitable material(s) and in any suitable manner. The housing 312 can also have any suitable shape or arrangement.

In this example, the locking rings 304-306 have more of a cylindrical shape (although it need not have a true cylindrical shape and can, for example, have slanted sides). That is, the major surface of each locking ring 304-306 extends along and rotates around a central axis through the center of that locking ring 304-306.

Although FIGS. 1A through 3C illustrate three examples of ocular fixation devices, various changes may be made to FIGS. 1A through 3C. For example, the relative sizes and dimensions of the features of the ocular fixation devices are for illustration only and can be altered in any suitable manner. Also, various features shown and described with respect to one of the ocular fixation devices could be used with other ocular fixation devices. As a particular example, the locking rings 206-208 of the ocular fixation device 200 could be used with the ocular fixation device 100. As another particular example, the same or similar housing 312 used with the ocular fixation device 300 could be used with the other ocular fixation devices 100 and 200. In addition, the dome could be omitted from an ocular fixation device, such as when the ocular fixation device is used to secure a patient's eye during corneal surgery or other surgical procedure.

FIGS. 4A through 4I illustrate an example use of an ocular fixation device during creation of a scleral tunnel for receiving a scleral prosthesis in accordance with this disclosure. The example use shown in FIGS. 4A through 4I is for illustration only. An ocular fixation device could be used in any other suitable manner (including only to fixate a patient's eye) without departing from the scope of this disclosure.

As shown in FIGS. 4A through 4I, a surgical tool 450 is used, in conjunction with an ocular fixation device 400, to form incisions in a patient's eye. In this example, the ocular fixation device 400 represents the ocular fixation device 300, although any other suitable ocular fixation device could be used.

Figure 4A:
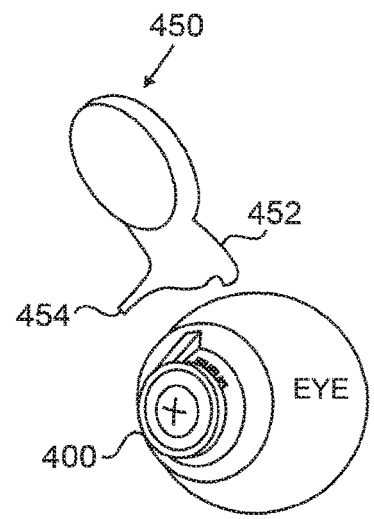
FIGS. 4A through 4I illustrate an example use of an ocular fixation device during creation of a scleral tunnel for receiving a scleral prosthesis in accordance with this disclosure.
Figure 4B:
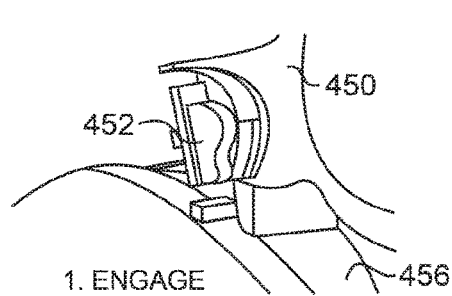
Figure 4C:
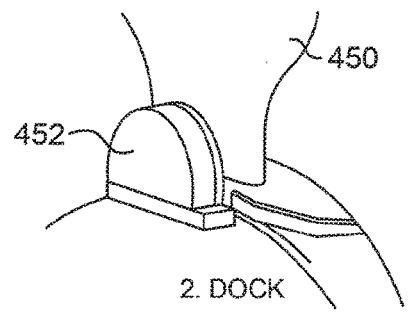
Figure 4D:
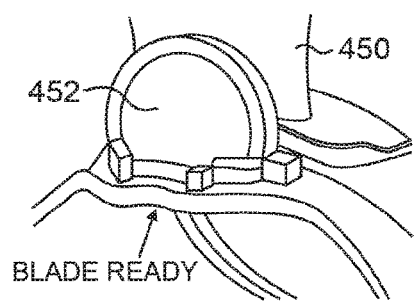
Figure 4E:
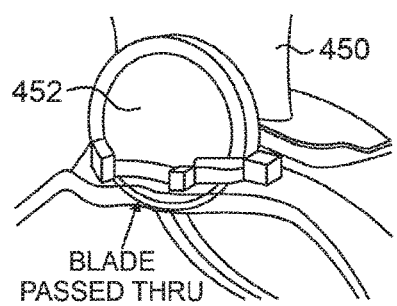

In this example, the surgical tool 450 includes a surgical blade 452 and a connecting portion 454. As shown in FIGS. 4A through 4C, the connecting portion 454 of the surgical tool 450 can engage connection points 456 of a housing associated with the ocular fixation device 400, thereby mounting the surgical tool 450 on the ocular fixation device 400. After that, as shown in FIGS. 4B through 4E, the surgical tool 450 can be rotated into position, and the surgical blade 452 can be rotated into and out of the patient's sclera to form a scleral tunnel. This process could then be repeated by mounting the surgical tool 450 at a different connection point 456. As a particular example, four scleral tunnels could be formed in a patient's eye using this technique.

In some embodiments, the surgical tool 450 is removed from the ocular fixation device 400 after one or more scleral tunnels have been formed but before one or more scleral prostheses are implanted in the tunnels. The ocular fixation device 400 could also be removed from the patient's eye before or after the scleral prostheses are implanted in the scleral tunnels.

In other embodiments, the ocular fixation device 400 and the surgical tool 450 could be used to facilitate implantation of a scleral prosthesis in a scleral tunnel. For example, as shown in FIGS. 4F through 4I, the surgical tool 450 could be configured to deposit a scleral prosthesis into a scleral tunnel during formation of the scleral tunnel. In this example, the surgical blade 452 includes a central portion 460, a curved cutting blade 462, and two hub arms 464a-464b. The central portion 460 is connected to the surgical tool 450 and can be rotated in multiple directions to move the cutting blade 462 into and out of the scleral tissue of a patient's eye. The hub arms 464a-464b couple the central portion 460 to the cutting blade 462, helping to translate rotation of the central portion 460 into movement of the cutting blade 462.

Figure 4F:
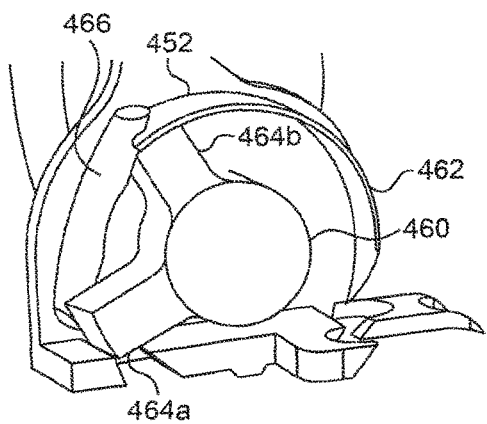
Figure 4G:
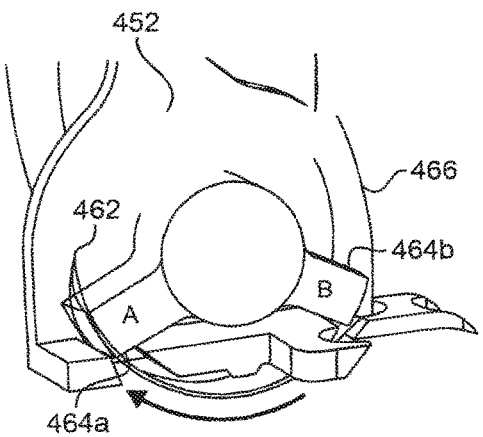
Figure 4H:
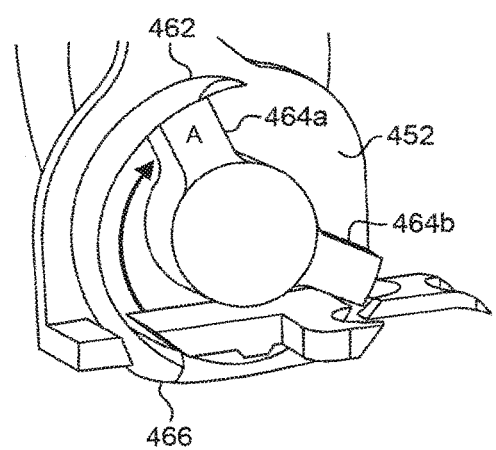
Figure 4I:
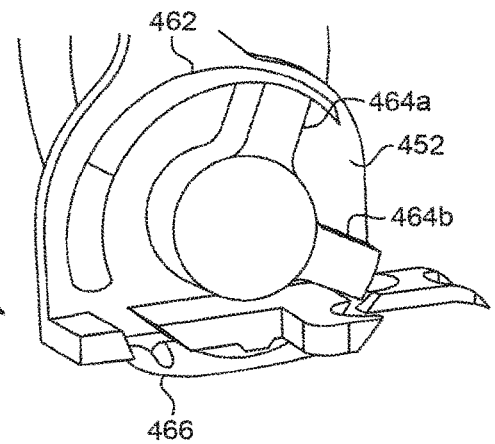

A prosthesis 466 is engaged with the tail end of the cutting blade 462. The prosthesis 466 could represent any suitable prosthesis, such as any of the prostheses disclosed in the above-incorporated patent documents. As shown in FIGS. 4F and 4G, the cutting blade 462 is initially rotated through the scleral tissue of a patient's eye using the hub arm 464b. Eventually, the hub arm 464a engages with the tip of the cutting blade 462, and the hub arm 464b disengages from the cutting blade 462. As shown in FIGS. 4H and 4I, the hub arm 464a then continues to rotate the cutting blade 462 through the scleral tissue and out of the newly formed scleral tunnel. In this example, the prosthesis 466 is pulled into the scleral tunnel upside-down by the surgical blade 452 and disengages from the cutting blade 462. The prosthesis 466 can then be rotated to properly position the prosthesis 466 in the newly-formed scleral tunnel.

The technique shown in FIGS. 4F through 4I is for illustration only. Any other suitable technique could be used to implant a scleral prosthesis into a scleral tunnel, whether or not the implantation occurs using an ocular fixation device or a surgical tool mounted on an ocular fixation device.

Although FIGS. 4A through 4I illustrate one example use of an ocular fixation device during creation of a scleral tunnel for receiving a scleral prosthesis, various changes may be made to FIGS. 4A through 4I. For example, the surgical tool 450 could be attached to or mounted on the ocular fixation device 400 in any suitable manner. Also, the same or similar techniques could be used to form incisions in other portions of a patient's eye. In addition, any other suitable surgical tool could be used in conjunction with an ocular fixation device, or no surgical tool could be used with an ocular fixation device.

Figure 5A:
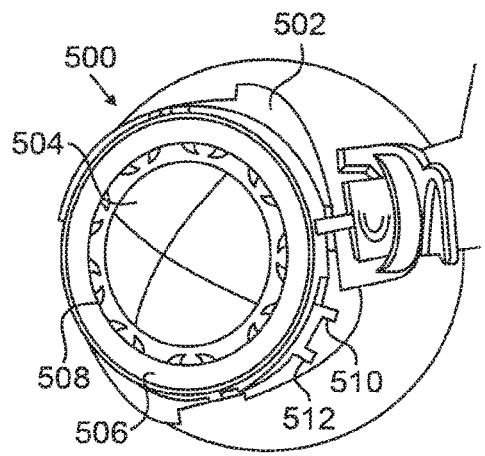
FIGS. 5A through 5C illustrate a fourth example ocular fixation device and an example use of the ocular fixation device in accordance with this disclosure.
Figure 5B:
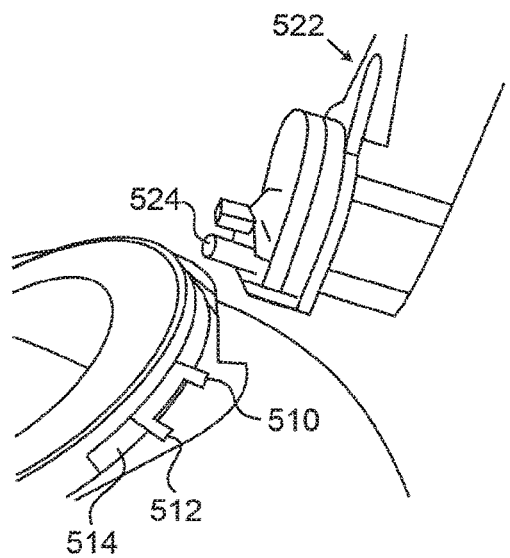
Figure 5C:
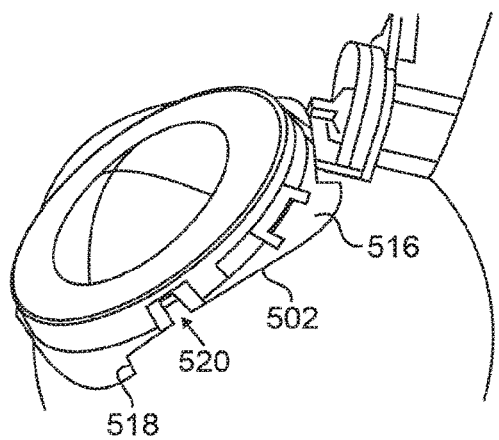

FIGS. 5A through 5C illustrate a fourth example ocular fixation device 500 and an example use of the ocular fixation device 500 in accordance with this disclosure. The embodiment of the ocular fixation device 500 and its use shown in FIGS. 5A through 5C are for illustration only. Other embodiments of the ocular fixation device 500 and uses of the ocular fixation device 500 could be used without departing from the scope of this disclosure.

As shown in FIG. 5A, the ocular fixation device 500 is similar to the ocular fixation device 200 of FIGS. 2A through 2C. The ocular fixation device 500 includes a base 502, a dome 504, and locking rings 506-508. In this example, the base 502 is attached or secured to the dome 504 (or vice versa), and the locking rings 506-508 are secured between the base 502 and the dome 504.

In this example embodiment, the locking rings 506-508 include tabs 510-512, respectively. The tabs 510-512 extend outside of the base 502 and the dome 504. For example, as shown in FIG. 5B, one or more gaps 514 could exist between the base 502 and the dome 504, and the tabs 510-512 may extend through one or more of the gaps 514. The tabs 510-512 can be used to control the opening and closing of the teeth on the locking rings 506-508. For instance, the tabs 510-512 can be pulled apart to open the teeth on the locking rings 506-508, and the tabs 510-512 can be pushed together to close the teeth on the locking rings 506-508.

As shown here, the base 502 of the ocular fixation device 500 includes portions 516 that project from the main body of the ocular fixation device 500 and that are arranged to lie generally on a patient's eye. The portions 516 include straight edges or guides 518, and the base 502 also includes notches 520. The guides 518 and the notches 520 are used to align a surgical tool 522 during a surgical procedure. For example, the surgical tool 522 could include a projection 524, which can be inserted into each of the notches 520 of the ocular fixation device 500. Also, the surgical tool 522 can be positioned so that its base is aligned with one of the straight guides 518 of the ocular fixation device 500. The surgical tool 522 can then be used to form an incision in the patient's eye, such as a scleral tunnel for receiving a scleral prosthesis. In this particular example, the ocular fixation device 500 includes guides 518 and notches 520 in four locations, although any other suitable number of locations could be supported.

In this way, the ocular fixation device 500 serves to secure the position of the patient's eye during a surgical procedure. At the same time, the ocular fixation device 500 facilitates the placement of the surgical tool 522 in the appropriate locations on the patient's eye.

Although FIGS. 5A through 5C illustrate a fourth example of an ocular fixation device 500 and an example use of the ocular fixation device 500, various changes may be made to FIGS. 5A through 5C. For example, the relative sizes and dimensions of the features of the ocular fixation device 500 are for illustration only and can be altered in any suitable manner. Also, the guide mechanisms described above (the straight guides 518 and the notches 520) could be used with any other ocular fixation device and any other surgical tool.

Figure 6A:
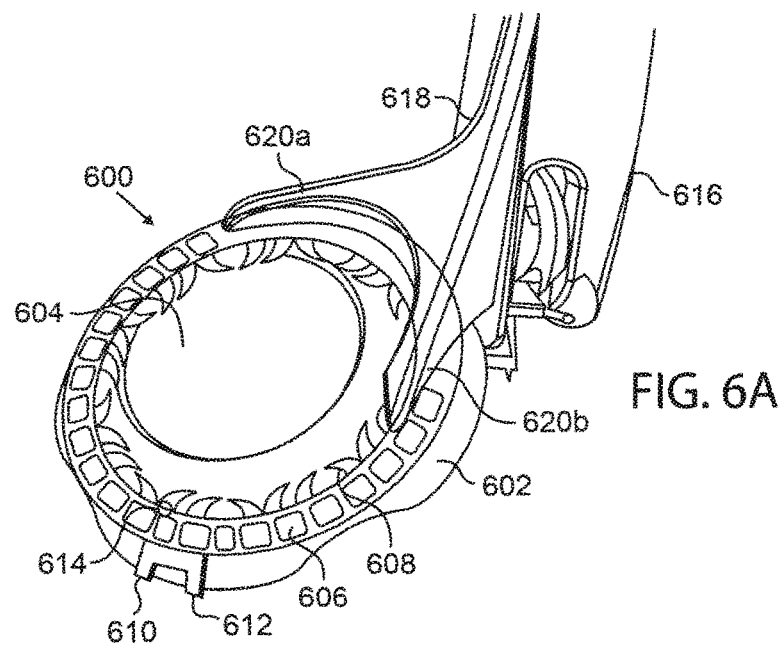
FIGS. 6A through 6C illustrate a fifth example ocular fixation device and an example use of the ocular fixation device in accordance with this disclosure.
Figure 6B:
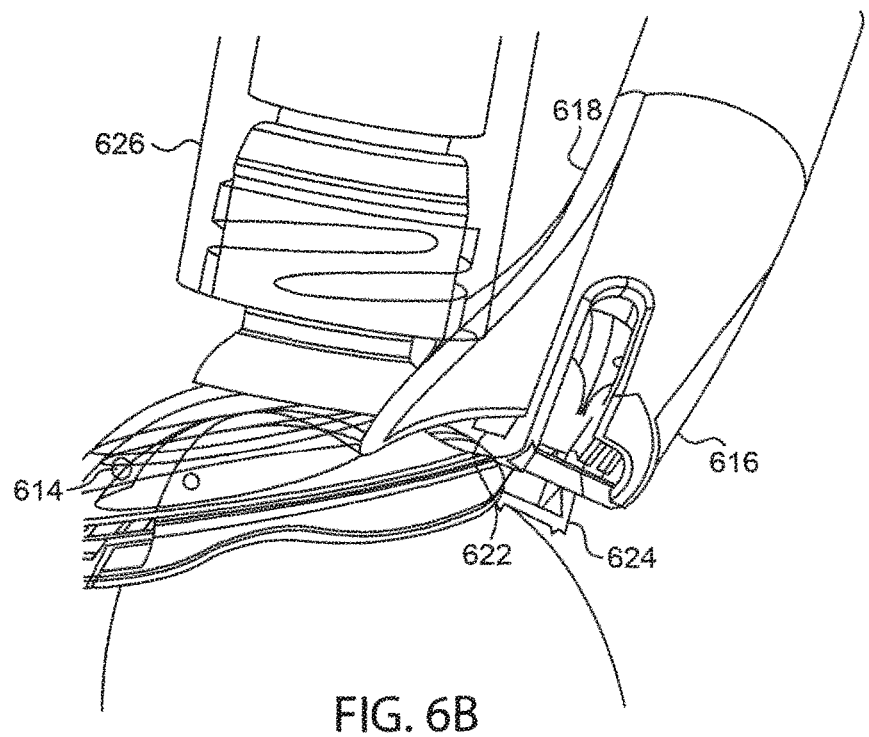
Figure 6C:
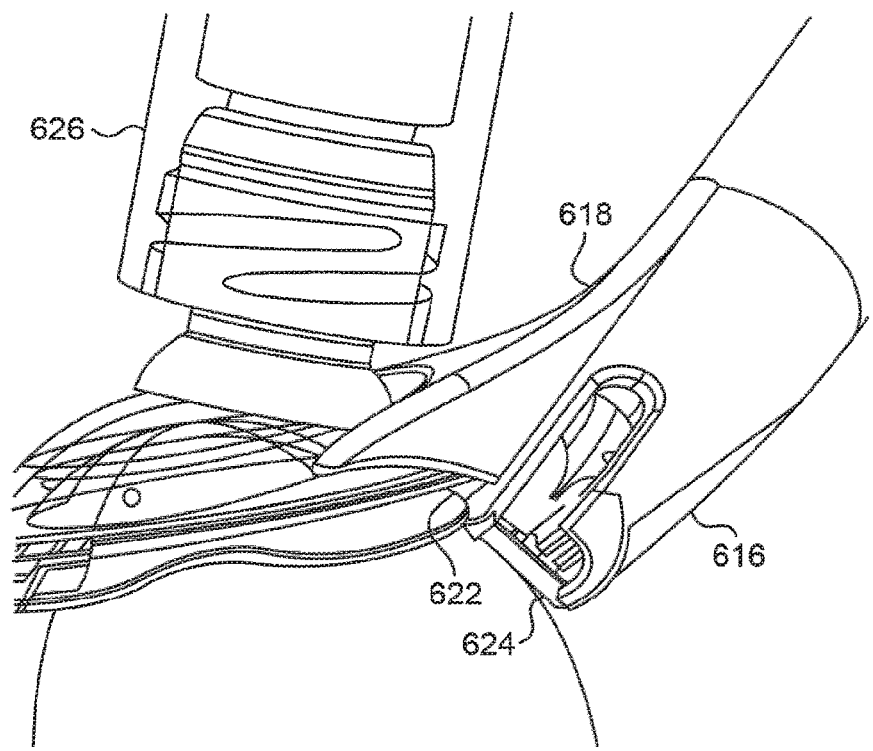

FIGS. 6A through 6C illustrate a fifth example ocular fixation device 600 and an example use of the ocular fixation device 600 in accordance with this disclosure. The embodiment of the ocular fixation device 600 and its use shown in FIGS. 6A through 6C are for illustration only. Other embodiments of the ocular fixation device 600 and uses of the ocular fixation device 600 could be used without departing from the scope of this disclosure.

As shown in FIG. 6A, the ocular fixation device 600 is similar to other ocular fixation devices described above. The ocular fixation device 600 includes a base 602, a dome 604, and locking rings 606-608. In this example, the base 602 is attached or secured to the dome 604 (or vice versa), and the locking rings 606-608 are secured between the base 602 and the dome 604. In this particular example, the locking ring 606 includes multiple sets of teeth (which could have different heights from the surface of a patient's eye), and these teeth correspond to multiple sets of teeth of the locking ring 608. As with the ocular fixation device 500, the locking rings 606-608 also include tabs 610-612, respectively, which extend outside of the base 602 and the dome 604 and can be used to control the opening and closing of the teeth on the locking rings 606-608.

As shown here, the dome 604 of the ocular fixation device 600 includes holes 614. The holes 614 in this example are used to align a surgical tool 616 to one or more locations of a patient's eye. The surgical tool 616 includes an alignment portion 618, which has two extensions 620a-620b forming a partial circle around the ocular fixation device 600. Each of the extensions 620a-620b includes an end that can be inserted into one of the holes 614 of the ocular fixation device 600. As shown in FIGS. 6B and 6C, the alignment portion 618 of the surgical tool 616 also includes a stopper 622, which can be depressed against the base 602 of the ocular fixation device 600. Collectively, the ends of the extensions 620a-620b and the stopper 622 represent three points that can be used to ensure the proper positioning of the surgical tool 616 on the patient's eye.

In this example, the surgical tool 616 includes two rotatable grasping clasps 624. As shown in FIG. 6B, the grasping clasps 624 could be opened before the surgical tool 616 is pressed onto the patient's eye. As shown in FIG. 6C, when the surgical tool 616 is pressed onto the patient's eye, the grasping clasps 624 rotate (either inward or outward). This helps to secure the surgical tool 616 in place on the patient's eye.

In this example embodiment, the extensions 620a-620b of the surgical tool 616 form a partial circle around the ocular fixation device 600. This allows the surgical tool 616 to be attached or mounted to the ocular fixation device 600 while leaving a large portion of the dome 604 exposed. Among other things, this may allow the use of a positioning tool 626, which can be used to place the ocular fixation device 600 into one or more positions on the patient's eye. Additional details regarding an example positioning tool are provided below.

Although FIGS. 6A through 6C illustrate a fifth example of an ocular fixation device 600 and an example use of the ocular fixation device 600, various changes may be made to FIGS. 6A through 6C. For example, the relative sizes and dimensions of the features of the ocular fixation device 600 are for illustration only and can be altered in any suitable manner. Also, the guide mechanisms described above (the holes 614 in the dome 604 and the alignment portion 618 of the surgical tool 616) could be used with any other ocular fixation device and any other surgical tool.

Figure 7:
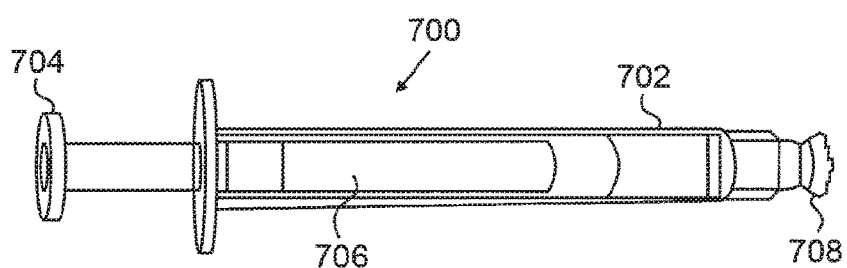
FIG. 7 illustrates an example positioning tool for use with an ocular fixation device in accordance with this disclosure.

FIG. 7 illustrates an example positioning tool 700 for use with an ocular fixation device in accordance with this disclosure. The embodiment of the positioning tool 700 shown in FIG. 7 is for illustration only. Other embodiments of the positioning tool 700 could be used without departing from the scope of this disclosure.

In this example embodiment, the positioning tool 700 represents a syringe structure having a body 702, a plunger 704 inserted into the body 702, a spring 706, and a suction cup 708. The spring 706 biases the plunger 704 in the open position, meaning the spring 706 pushes the plunger 704 away from the suction cup 708 at the end of the body 702. The end of the plunger 704 can form an air-tight seal within the body 702, and the suction cup 708 can form an air-tight seal with an ocular fixation device.

To place an ocular fixation device on a patient's eye, the plunger 704 can be depressed, such as by a surgeon or other personnel. The suction cup 708 can be placed on the ocular fixation device, such as on the dome of any of the ocular fixation devices described above. The spring 706 is then allowed to push the plunger 704 away from the suction cup 708. The air-tight seals create a vacuum within the body 702 of the positioning tool 700, causing the suction cup 708 to attach to the ocular fixation device. The ocular fixation device can therefore be picked up, moved, and placed in the appropriate position on a patient's eye using the positioning tool 700. Once in the appropriate position (and possibly after the ocular fixation device has been attached to the patient's eye), the plunger 704 can be depressed. This releases the suction cup 708 from the ocular fixation device.

This type of positioning tool 700 represents only one example of the types of tools that could be used to position an ocular fixation device. Any other suitable mechanism could be used to position an ocular fixation device. For example, an ocular fixation device could include a handle, such as a flip-ring that can be used to pick up the ocular fixation device and that can be rotated to the side and laid on the dome or base of the ocular fixation device. Any other suitable handle or other mechanism could be used to allow the ocular fixation device to be handled and positioned.

Although FIG. 7 illustrates one example of a positioning tool 700 for use with an ocular fixation device, various changes may be made to FIG. 7. For example, any other suitable device or technique could be used to place an ocular fixation device on a patient's eye.

Figure 8:
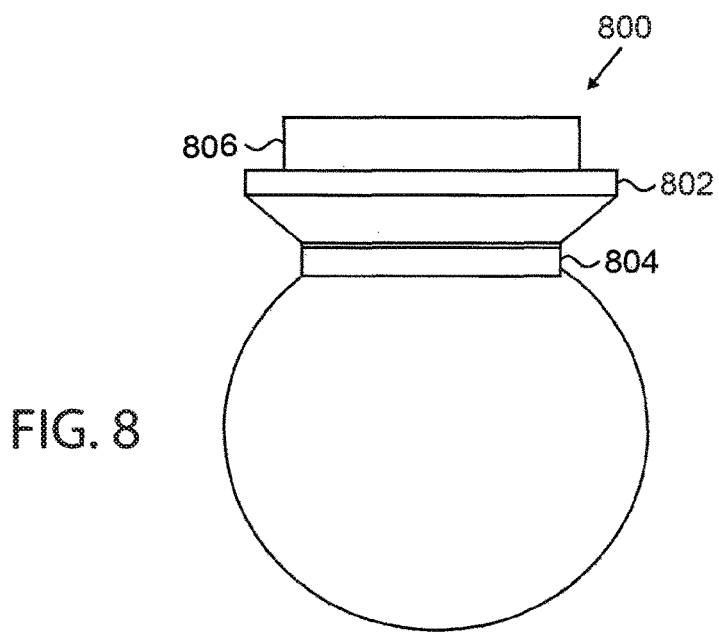
FIG. 8 illustrates a sixth example ocular fixation device in accordance with this disclosure.

FIG. 8 illustrates a sixth example ocular fixation device 800 in accordance with this disclosure. The embodiment of the ocular fixation device 800 shown in FIG. 8 is for illustration only. Other embodiments of the ocular fixation device 800 could be used without departing from the scope of this disclosure.

In this example, the ocular fixation device 800 includes a base 802, a fixation mechanism 804, and a handle 806. The base 802 may generally be pressed against a patient's eye, such as by pressing the base 802 down on the patient's cornea. The fixation mechanism 804 can then be attached to the patient's sclera, fixing the tool 800 in place and providing clear access to the patient's sclera. The fixation mechanism 804 could use any suitable technique to latch onto the patient's eye, such as prongs that can be forced into the patient's scleral tissue. The handle 806 can be used to raise and lower the fixation mechanism 804 after the base 802 has been pressed onto the patient's eye.

Although FIG. 8 illustrates a sixth example ocular fixation device 800, various changes may be made to FIG. 8. For example, any suitable mechanisms could be used to attach or otherwise associate the ocular fixation device 800 to the patient's eye.

Figures 9A, 9B:
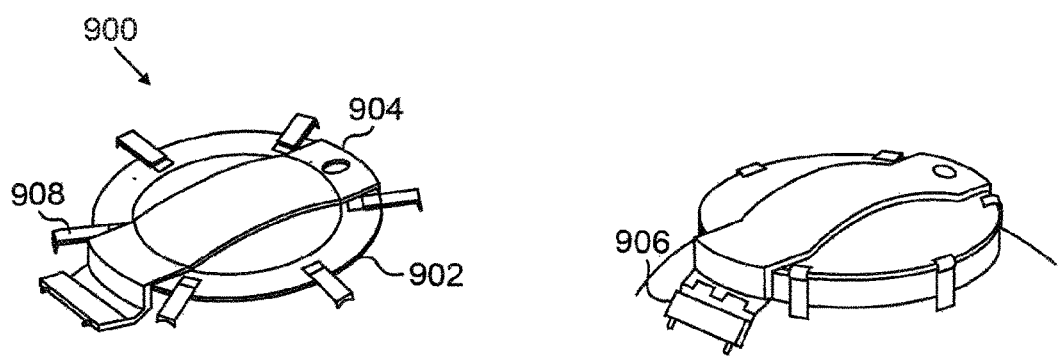
FIGS. 9A through 9C illustrate a seventh example ocular fixation device and an example use of the ocular fixation device in accordance with this disclosure.
Figure 9C:
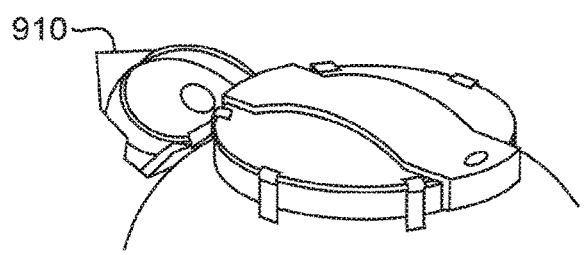

FIGS. 9A through 9C illustrate a seventh example ocular fixation device 900 and an example use of the ocular fixation device 900 in accordance with this disclosure. The embodiment of the ocular fixation device 900 and its use shown in FIGS. 9A through 9C are for illustration only. Other embodiments of the ocular fixation device 900 and uses of the ocular fixation device 900 could be used without departing from the scope of this disclosure.

As shown in FIGS. 9A through 9C, the ocular fixation device 900 includes a central portion 902, a support 904 having a tool connection 906, and prongs 908. In some embodiments, the central portion 902 of the ocular fixation device 900 generally fits over the patient's cornea or some other portion of the patient's eye. The central portion 902 of the ocular fixation device 900 may also be centered on the patient's eye. The support 904 may be removably attached to the central portion 902, and the tool connection 906 allows a surgical tool 910 to be attached to the support 904.

The prongs 908 hold the central portion 902 of the ocular fixation device 900 in place on the patient's eye. For example, the prongs 908 could be extended out as shown in FIG. 9A prior to placement on the patient's eye. The prongs 908 could then be pushed or rotated so that the ends of the prongs 908 attach or secure to the patient's eye.

In particular embodiments, the support 904 can be attached in one orientation to the central portion 902, the surgical tool 910 can be attached to the support 904, and a scleral tunnel can be formed. This process could then be repeated, with the support 904 being removed and attached in a different orientation to the central portion 902 so that the surgical tool 910 can form a scleral tunnel at another location on the patient's eye.

Although FIGS. 9A through 9C illustrate a seventh example ocular fixation device 900 and an example use of the ocular fixation device 900, various changes may be made to FIGS. 9A through 9C. For example, the ocular fixation device 900 could include other mechanisms for attachment to the patient's eye or to a surgical tool 910.

FIGS. 10A through 10D illustrate an eighth example ocular fixation device 1000 in accordance with this disclosure. The embodiment of the ocular fixation device 1000 shown in FIGS. 10A through 10D is for illustration only. Other embodiments of the ocular fixation device 1000 could be used without departing from the scope of this disclosure.

Figure 10A:
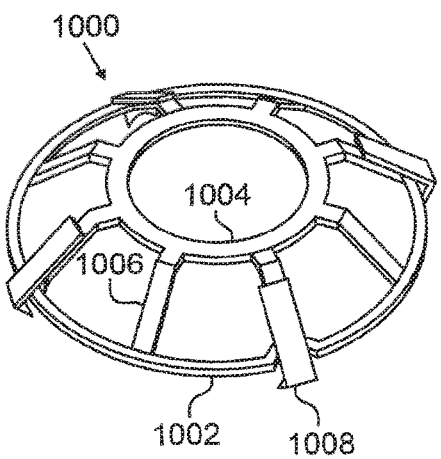
FIGS. 10A through 10D illustrate an eighth example ocular fixation device in accordance with this disclosure.

In this example, the ocular fixation device 1000 includes an outer ring 1002, an inner ring 1004, and ring connections 1006. The outer and inner rings 1002-1004 represent generally circular-shaped structures. As shown in FIG. 10A, the outer ring 1002 is generally in a different plane than the smaller inner ring 1004. The ring connections 1006 generally couple the outer and inner rings 1002-1004 together, forming an integrated structure. The ring connections 1006 are shaped such that a portion of a patient's eye can fit through the outer ring 1002 and approach or contact the inner ring 1004.

Figure 10B:
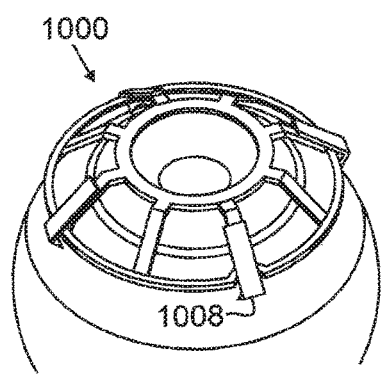
Figure 10C:
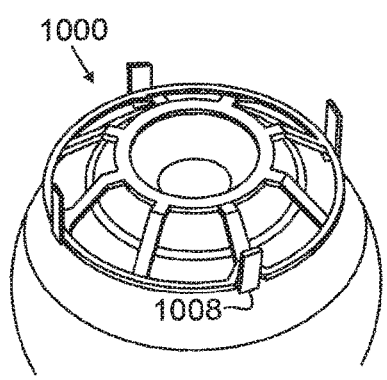
Figure 10D:
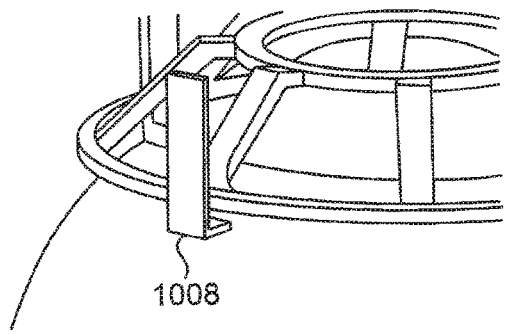

As shown here, the ocular fixation device 1000 also includes multiple prongs 1008, which are rotatably coupled to the outer ring 1002. As shown in FIG. 10B, the prongs 1008 can be opened prior to placement of the ocular fixation device 1000 on the patient's eye. As shown in FIGS. 10C and 10D, once placed on the patient's eye, each of the prongs 1008 can be rotated such that the ends of the prongs 1008 attach or secure to the patient's eye. To release the ocular fixation device 1000, the prongs 1008 can be rotated again to remove the ends of the prongs 1008 from the patient's eye.

Although FIGS. 10A through 10D illustrate an eighth example ocular fixation device 1000, various changes may be made to FIGS. 10A through 10D. For example, the rings 1002-1004 could have any suitable dimensions, and the inner ring 1004 could have any suitable distance from the outer ring 1002. Also, any suitable mechanisms could be used to couple the rings 1002-1004 together and to attach or otherwise associate the ocular fixation device 1000 to the patient's eye.

Figure 11A:
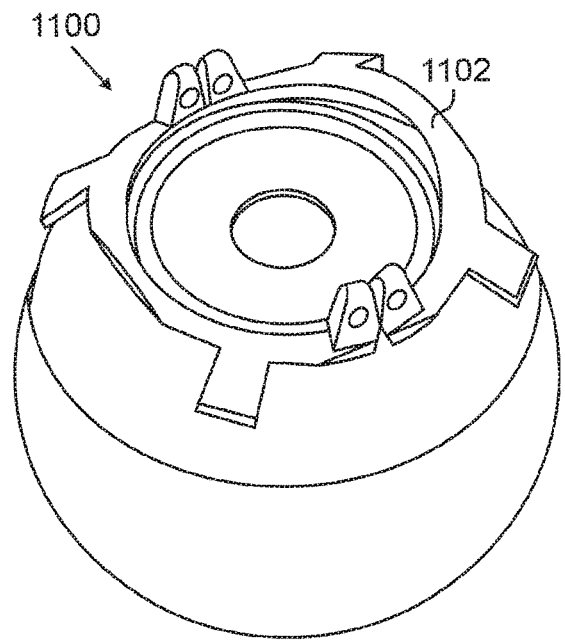
FIGS. 11A and 11B illustrate a ninth example ocular fixation device in accordance with this disclosure.
Figure 11B:
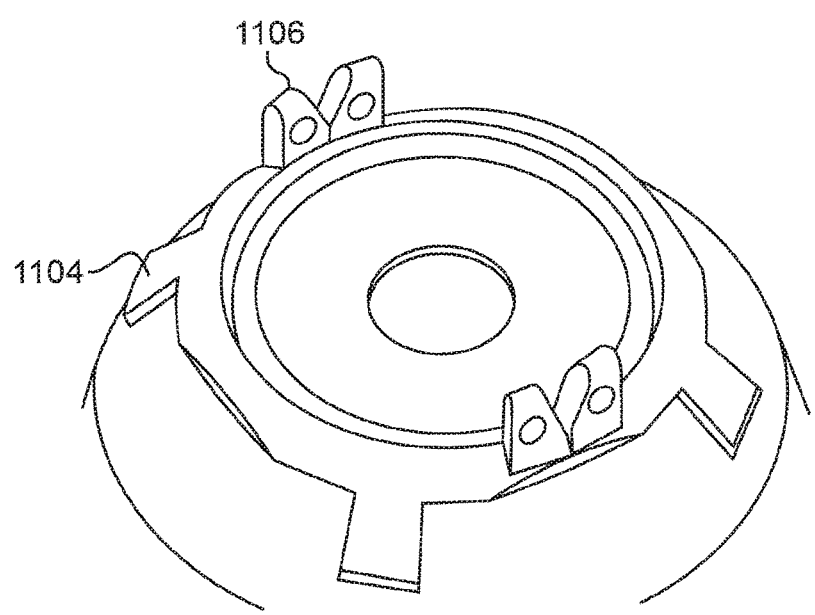

FIGS. 11A and 11B illustrate a ninth example ocular fixation device 1100 in accordance with this disclosure. The embodiment of the ocular fixation device 1100 shown in FIGS. 11A and 11B is for illustration only. Other embodiments of the ocular fixation device 1100 could be used without departing from the scope of this disclosure.

In this example, the ocular fixation device 1100 is formed from two rotatable segments 1102. Each segment 1102 includes prongs 1104 that can fix the segment 1102 to a patient's eye, such as in the sclera of the eye. Each segment 1102 also includes connection points 1104, which represent areas where other components (such as a surgical tool) can be attached to the ocular fixation device 1100. In addition, the ocular fixation device 1100 can provide reference markers identifying where scleral tunnels should be formed in the patient's eye, such as at locations at or between the prongs 1104. In some embodiments, one of the segments 1102 can be attached to the patient's eye, and then the other segment 1102 can be rotated out and attached to the patient's eye.

Although FIGS. 11A and 11B illustrate a ninth example ocular fixation device 1100, various changes may be made to FIGS. 11A and 11B. For example, each rotatable segment 1102 could include any suitable number of prongs 1104.

Figure 12A:
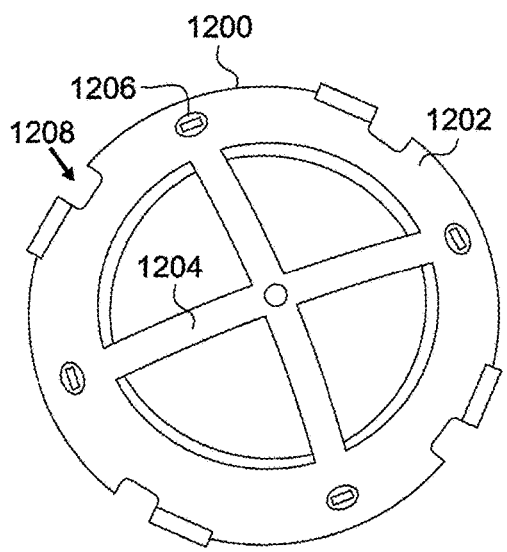
FIGS. 12A and 12B illustrate a tenth example ocular fixation device in accordance with this disclosure.
Figure 12B:
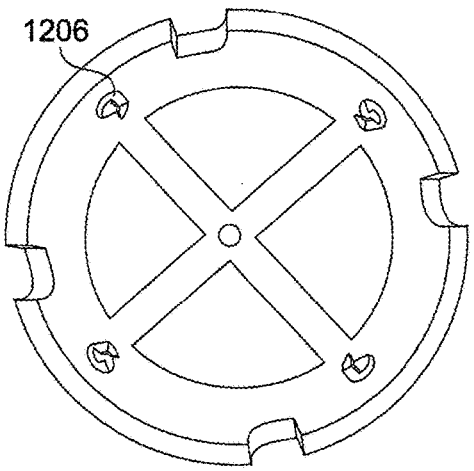
Figure 18A:
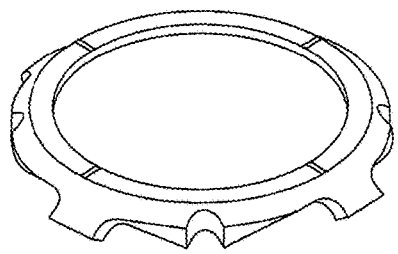
FIGS. 18A and 18B illustrate a conventional ocular fixation tool.
Figure 18B:
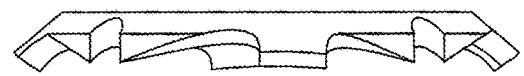

FIGS. 12A and 12B illustrate a tenth example ocular fixation device 1200 in accordance with this disclosure. The embodiment of the ocular fixation device 1200 shown in FIGS. 12A and 12B is for illustration only. Other embodiments of the ocular fixation device 1200 could be used without departing from the scope of this disclosure.

In this example, the ocular fixation device 1200 generally includes a ring 1202 with crossbars 1204. The ring 1202 is generally sized and shaped to lie on a patient's eye, such as by having a slanted inner edge that generally lies on the sclera of the patient's eye. The crossbars 1204 are generally sized and shaped to allow a portion of the patient's eye to fit through the ring 1202 and approach or contact the crossbars 1204.

In this example embodiment, twist picks 1206 are provided along the ring 1202. The twist picks 1206 represent screw-type structures that can attach to and release the ocular tissue of the patient's eye. For example, rotating the twist picks 1206 in one direction may attach the twist picks 1206 to the ocular tissue of the patient's eye. Rotating the twist picks 1206 in the opposite direction may release the ocular tissue. In this way, the ring 1202 can be attached to the patient's eye through simple rotation of the twist picks 1206.

As shown here, the ocular fixation device 1200 also includes connection points 1208. The connection points 1208 generally represent areas where, for example, a surgical tool for forming scleral incisions can be mounted on the ocular fixation device 1200. In this example, each of the connection points 1208 includes an elevated area of the ring 1202 adjacent to a notch in the ring 1202. However, any other suitable mechanism could be used to mount or otherwise couple any suitable surgical tool to the ocular fixation device 1200.

Although FIGS. 12A and 12B illustrate a tenth example ocular fixation device 1200, various changes may be made to FIGS. 12A and 12B. For example, the ring 1202 and the crossbars 1204 could have any suitable shape or dimensions, and the crossbars 1204 could join at any suitable height above the ring 1202. Also, any suitable mechanisms could be used to attach or otherwise associate the ocular fixation device 1200 to the patient's eye.

FIGS. 13A through 13D illustrate an eleventh example ocular fixation device 1300 in accordance with this disclosure. The embodiment of the ocular fixation device 1300 shown in FIGS. 13A through 13D is for illustration only. Other embodiments of the ocular fixation device 1300 could be used without departing from the scope of this disclosure.

Figure 13A:
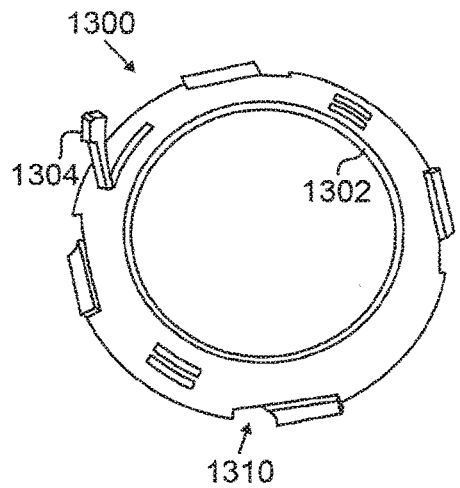
FIGS. 13A through 13D illustrate an eleventh example ocular fixation device in accordance with this disclosure.
Figure 13B:
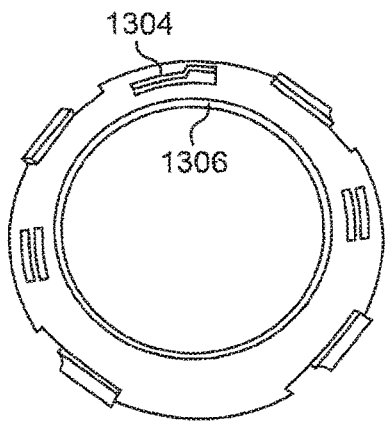
Figure 13C:
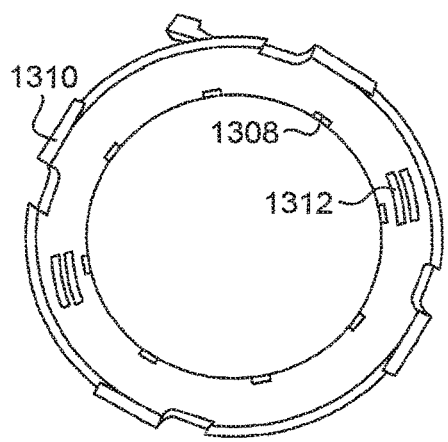
Figure 13D:
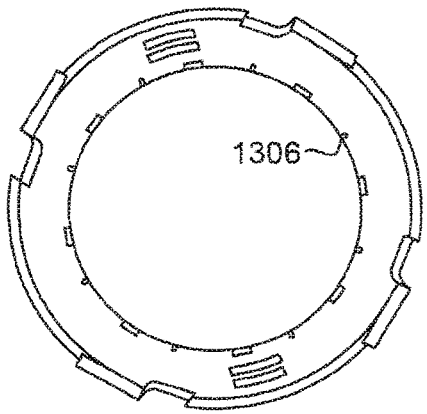

In this example, the ocular fixation device 1300 includes a ring 1302 having a lever 1304. The lever 1304 is used to control the movement of retractable pins 1306, which can be retracted into and extended out of the ring 1302. For example, the lever 1304 could be placed in the raised position as shown in FIG. 13A to retract the pins 1306 into the ring 1302. The ring 1302 could then be placed on the patient's eye and positioned properly. After that, the lever 1304 can be lowered as shown in FIG. 13B, causing the pins 1306 to extend from the ring 1302 and lock onto the patient's ocular tissue. For instance, the pins 1306 could penetrate the limbus of the patient's eye to a depth of 200 microns. Any suitable mechanism could be used to cause the pins 1306 to retract and extend under the control of the lever 1304.

In this example embodiment, the ocular fixation device 1300 could also include vertical teeth 1308, which may or may not penetrate the surface of the patient's eye. If the vertical teeth 1308 do not penetrate the surface of the patient's eye, the vertical teeth 1308 could still grip the patient's eye and provide lateral fixation, meaning the vertical teeth 1308 may help to prevent sideways motion of the ocular fixation device 1300 on the patient's eye. In addition, as with various prostheses described above, the ocular fixation device 1300 can include one or more connection points 1310 and one or more windows 1312.

Although FIGS. 13A through 13D illustrate an eleventh example ocular fixation device 1300, various changes may be made to FIGS. 13A through 13D. For example, the ring 1302, lever 1304, pins 1306, and other elements could have any suitable shape or dimensions. Also, any suitable mechanisms could be used to attach or otherwise associate the ocular fixation device 1300 to the patient's eye.

Figure 14A:
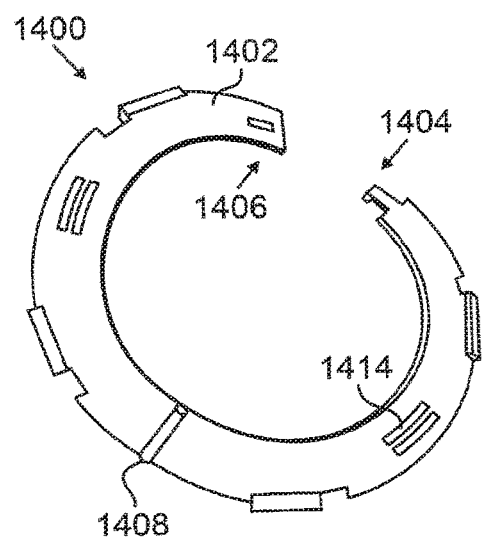
FIGS. 14A through 14C illustrate a twelfth example ocular fixation device in accordance with this disclosure.
Figure 14B:
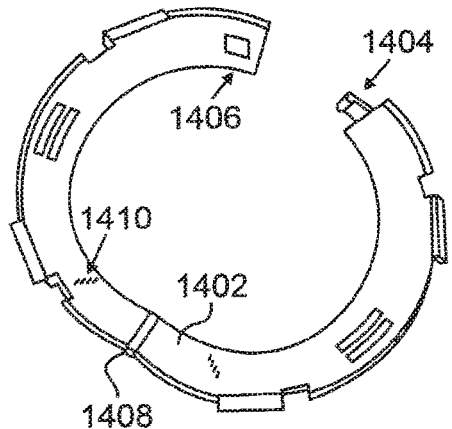
Figure 14C:
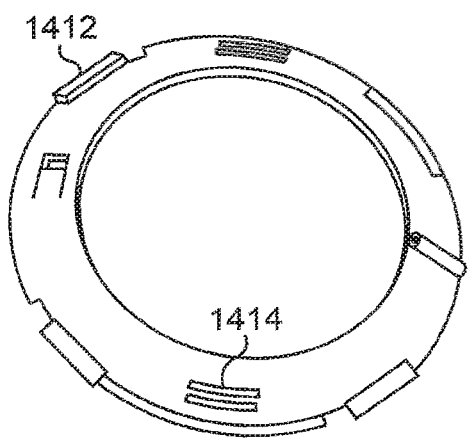

FIGS. 14A through 14C illustrate a twelfth example ocular fixation device 1400 in accordance with this disclosure. The embodiment of the ocular fixation device 1400 shown in FIGS. 14A through 14C is for illustration only. Other embodiments of the ocular fixation device 1400 could be used without departing from the scope of this disclosure.

In this example, the ocular fixation device 1400 includes a ring 1402 having a latch 1404 at one end and a receptacle 1406 at its other end. The ring 1402 also includes a hinge 1408, allowing two portions of the ring 1402 to open and close with respect to each other. In this embodiment, the portions of the ring 1402 can be pushed apart to open the ring 1402. The ring 1402 can be placed on a patient's eye, and the latch 1404 can be pushed into the receptacle 1406, forming a completed ring. As shown in FIG. 14B, the lower edge of the ring 1402 includes spikes 1410 that can dig into the ocular tissue of the patient's eye, securing the ring 1402 in place on the patient's eye.

As shown here, the ocular fixation device 1400 also includes connection points 1412, which generally represent areas where, for example, a surgical tool for forming scleral incisions can be mounted on the ocular fixation device 1400. Any suitable type of connection points or other mechanisms could be used to mount or otherwise couple any suitable surgical tool to the ocular fixation device 1400.

The ocular fixation device 1400 further includes one or more windows 1414. The windows 1414 allow a surgeon or other personnel to see through the ocular fixation device 1400 so as to determine the position of the ocular fixation device 1400 with respect to certain features of the patient's eye. For example, the windows 1414 could allow a surgeon to ensure that the ocular fixation device 1400 is attached to the area at or near the limbus of the patient's eye. The windows 1414 could have any suitable size, shape, and distribution in the ocular fixation device 1400.

Although FIGS. 14A through 14C illustrate a twelfth example ocular fixation device 1400, various changes may be made to FIGS. 14A through 14C. For example, the ring 1402, latch 1404, and receptacle 1406 could have any suitable shape or dimensions. Also, any suitable mechanisms could be used to attach or otherwise associate the ocular fixation device 1400 to the patient's eye.

Figure 15:
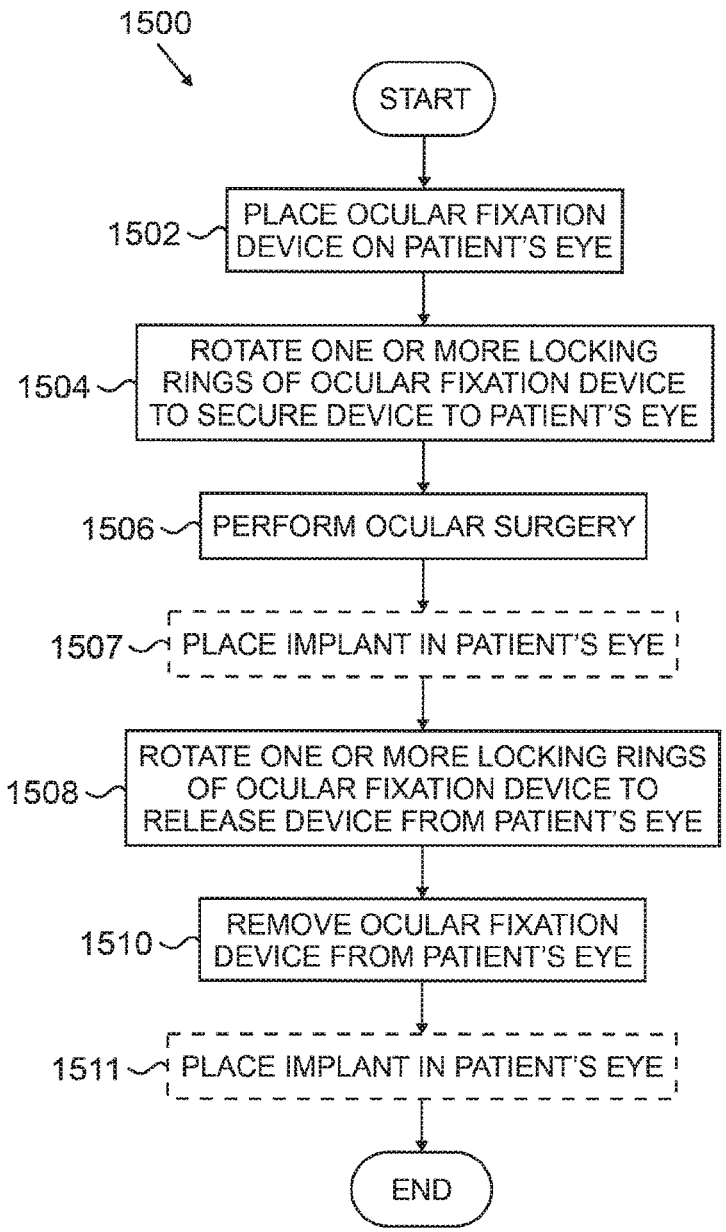
FIG. 15 illustrates an example method for ocular fixation in accordance with this disclosure.
Figure 16A:
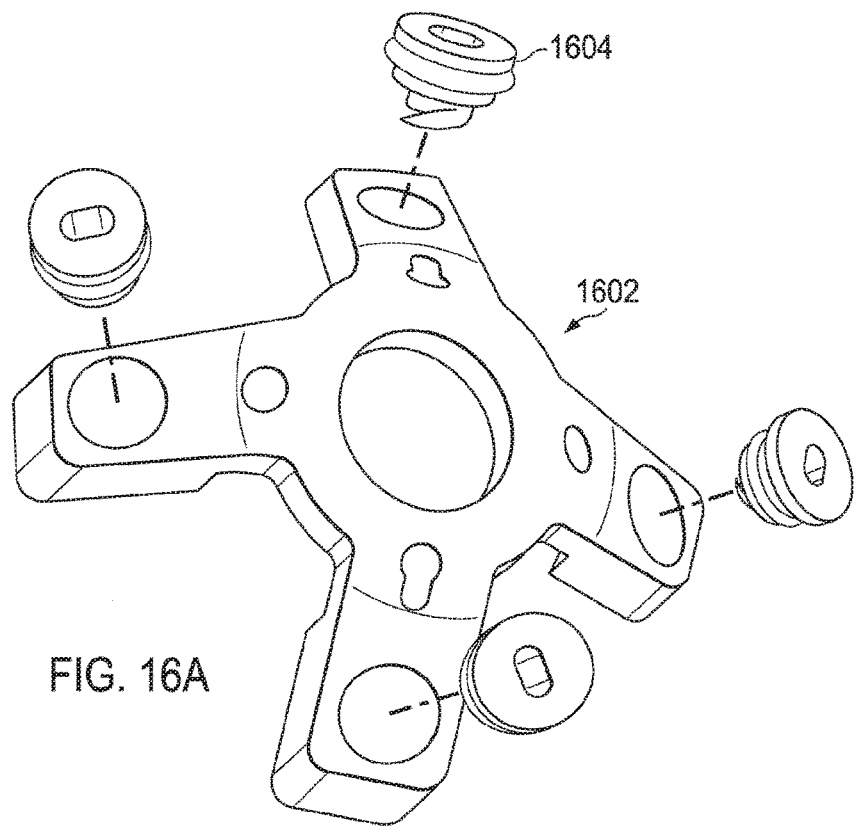
FIGS. 16A through 16D illustrate a thirteenth example ocular fixation device in accordance with this disclosure.
Figure 16B:
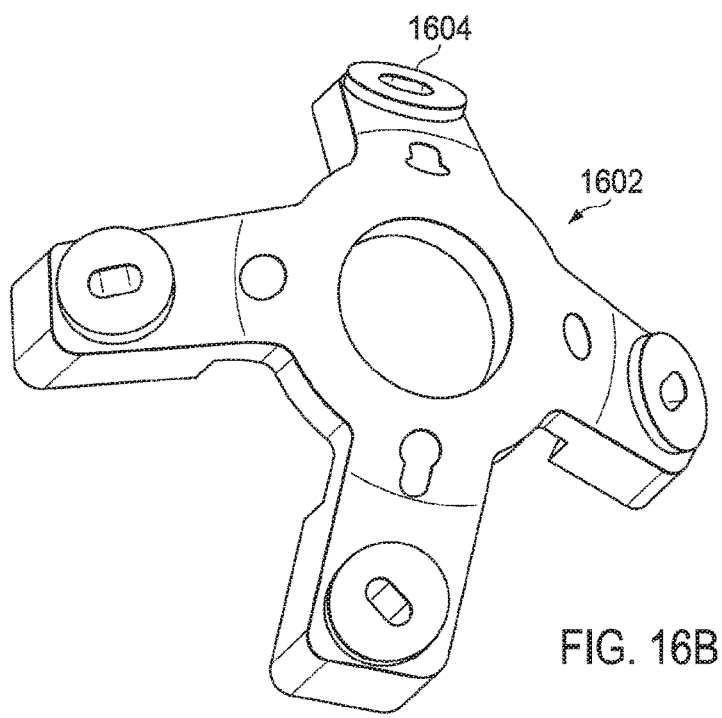
Figure 16C:
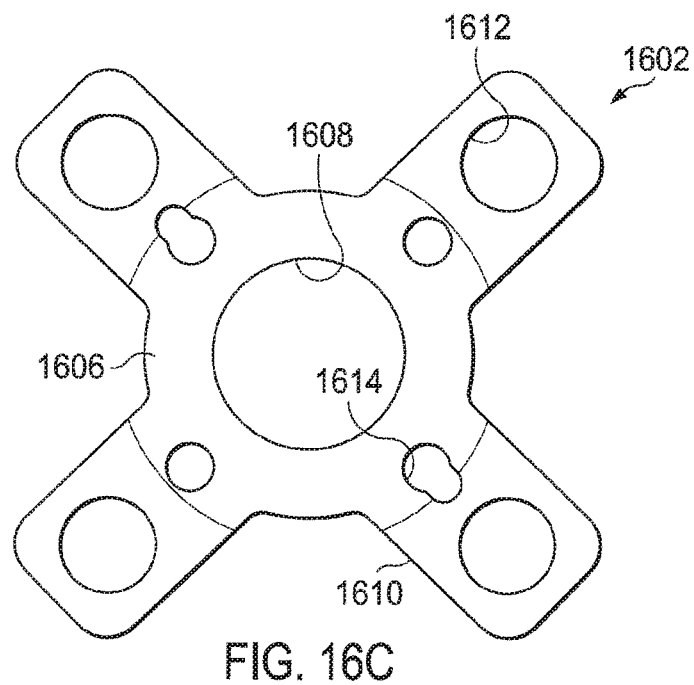
Figure 16D:
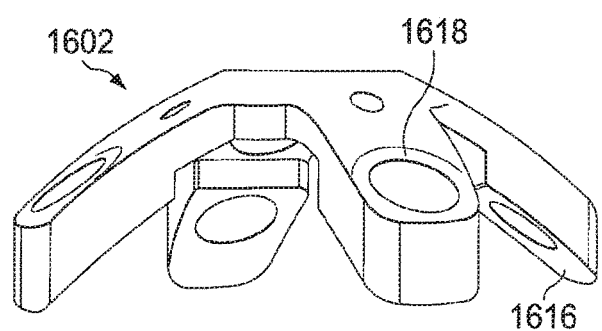

FIG. 15 illustrates an example method 1500 for ocular fixation in accordance with this disclosure. The embodiment of the method 1500 shown in FIG. 15 is for illustration only. Other embodiments of the method 1500 could be used without departing from the scope of this disclosure.

An ocular fixation device is placed on a patient's eye at step 1502. This could include, for example, placing any of the ocular fixation devices described above on the patient's eye. The ocular fixation device could include a dome so that the central portion of the patient's eye is covered and protected by the ocular fixation device.

One or more locking rings of the ocular fixation device are rotated to secure the ocular fixation device to the patient's eye at step 1504. This could include, for example, using an external tool to move one or more of the locking rings of the ocular fixation device. This could also include rotating one or more portions of the ocular fixation device to cause one or more of the locking rings to rotate. This could further include rotating one or more tabs coupled to one or more of the locking rings to cause one or more of the locking rings to rotate. Any other suitable technique could be used here to rotate one or more locking rings of the ocular fixation device.

An ocular surgical procedure occurs at step 1506. This could include, for example, forming one or more scleral tunnels in sclera of the patient's eye. Optionally, one or more scleral prostheses or other implants are placed in the patient's eye at step 1507. This could include, for example, inserting the scleral prostheses as the tunnels are being formed (as shown in FIGS. 4F through 4I above). This could also include inserting the scleral prostheses into the tunnels manually or otherwise after a surgical tool has been mounted on the ocular fixation device and used to form the scleral tunnels.

One or more locking rings of the ocular fixation device are rotated to release the ocular fixation device from the patient's eye at step 1508. This could include, for example, using an external tool, one or more portions of the ocular fixation device, or tabs coupled to the locking rings to rotate one or more of the locking rings. The ocular fixation device is removed from the patient's eye at step 1510. Optionally, one or more scleral prostheses or other implants are placed in the patient's eye at step 1511. This could include, for example, inserting the scleral prostheses into the tunnels manually or otherwise after the ocular fixation device has been removed from the patient's eye. One or both of the optional steps 1507 and 1511 show that the ocular fixation device can be used in a variety of ways during a surgical procedure.

Although FIG. 15 illustrates one example of a method 1500 for ocular fixation, various changes may be made to FIG. 15. For example, any suitable surgical procedure could involve the use of ocular fixation. Also, the surgical procedure may, but need not, involve the implantation of one or more scleral prostheses or other implants or elements into the patient's eye. Further, while described as rotating one or more locking rings to secure and release the patient's eye, other techniques (such as those associated with other embodiments of the ocular fixation devices described above) could be used.

FIGS. 16A through 16D illustrate a thirteenth example ocular fixation device 1600 in accordance with this disclosure. The embodiment of the ocular fixation device 1600 shown in FIGS. 16A through 16D is for illustration only. Other embodiments of the ocular fixation device 1600 could be used without departing from the scope of this disclosure.

In this example, the ocular fixation device 1600 generally includes a body 1602 and multiple twist picks 1604. The twist picks 1604 represent screw-type structures that can attach to and release the ocular tissue of a patient's eye. For example, rotating the twist picks 1604 in one direction may attach the twist picks 1604 to the ocular tissue of the patient's eye, thereby attaching the body 1602 to the patient's eye. Rotating the twist picks 1604 in the opposite direction may release the ocular tissue, thereby releasing the body 1602 from the patient's eye. In this way, the body 1602 can be attached to the patient's eye through simple rotation of the twist picks 1604.

As shown here, the body 1602 includes a central portion 1606 (such as a ring) that defines an opening 1608. The opening 1608 may allow, for example, the body 1602 to be centered on a patient's eye. Extending from the central portion 1606 are multiple bars or other projections 1610. Each projection 1610 includes an opening 1612 through which a twist pick 1604 can be inserted. The projections 1610 also include connection points 1614, which generally represent areas where, for example, a surgical tool for forming scleral incisions can be mounted on the ocular fixation device 1600. In this example, each of the connection points 1614 includes a circular opening or a circular opening with an adjacent smaller tab. However, any other suitable mechanism could be used to mount or otherwise couple any suitable surgical tool to the ocular fixation device 1600.

The body 1602 is generally sized and shaped to lie on a patient's eye, such as by having slanted inner edges 1616 that generally lie on the sclera of the patient's eye. Also, the top surface of the body 1602 around the openings 1612 have recessed areas 1618, which allow tops of the twist picks 1604 to be partially recessed within the body 1602 when the twist picks 1604 are inserted into the openings 1612.

In some embodiments, the body 1602 of the ocular fixation device 1600 is secured to ocular tissue of a patient's eye by placing the body 1602 on the eye and rotating each of the twist picks 1604 (such as by about 180°). At that point, a surgical tool can be mounted on the body 1602, and one or more incisions or other surgical operations could occur in one or more locations. Once completed, the surgical tool can be removed from the body 1602, the twist picks 1604 can be rotated in the opposite direction, and the body 1602 can be removed from the patient's eye.

Although FIGS. 16A through 16D illustrate a thirteenth example ocular fixation device 1600, various changes may be made to FIGS. 16A through 16D. For example, the body 1602 could have any suitable shape or dimensions. Also, any suitable mechanisms could be used to attach or otherwise associate the ocular fixation device 1600 to the patient's eye.

Figure 17A:
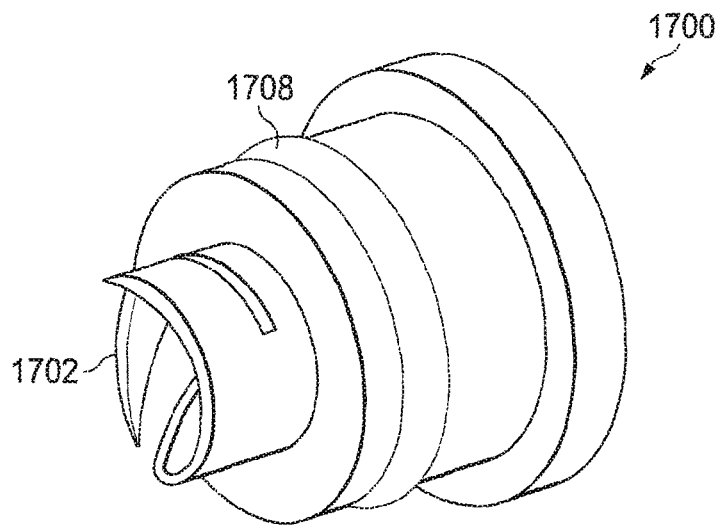
FIGS. 17A and 17B illustrate an example twist pick used in an ocular fixation device in accordance with this disclosure.
Figure 17B:
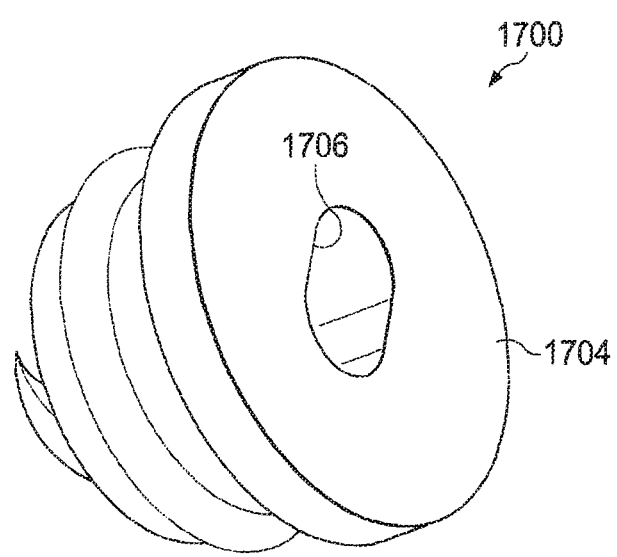
Figure 19:
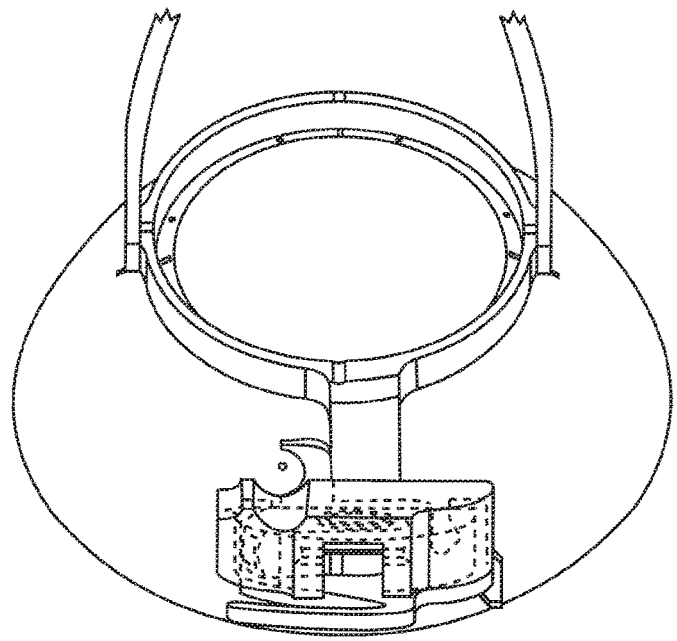
FIG. 19 illustrates a second conventional ocular fixation tool.
Figure 20A:
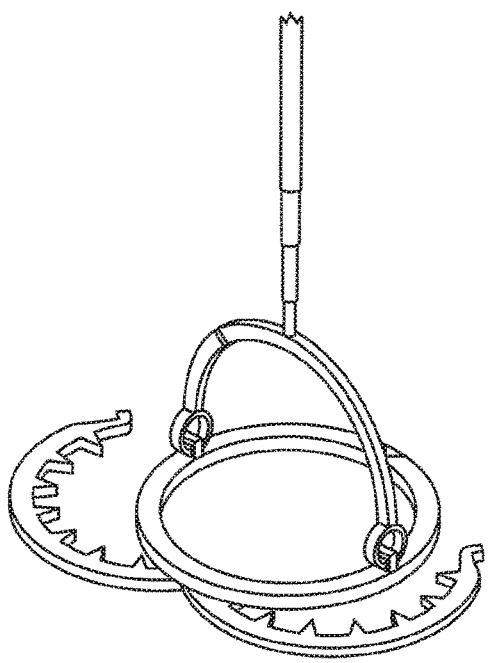
FIGS. 20A and 20B illustrate a third conventional ocular fixation tool.
Figure 20B:
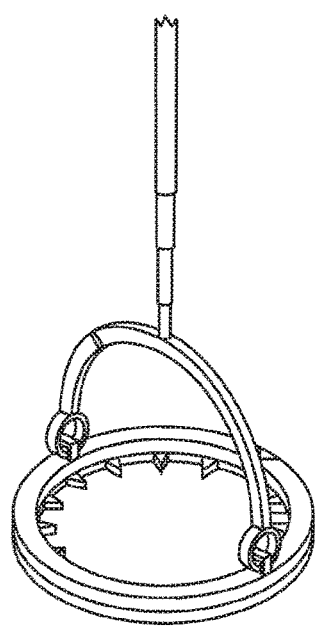

FIGS. 17A and 17B illustrate an example twist pick 1700 used in an ocular fixation device in accordance with this disclosure. The twist pick 1700 could, for example, be used with the ocular fixation devices 1200 and 1600. As shown here, the twist pick 1700 includes two teeth 1702 at the bottom of the twist pick 1700. The teeth 1702 here arch circumferentially around an axis of the twist pick 1700 and are roughly 180° apart. Rotation of the twist pick 1700 in one direction causes the teeth 1702 to dig into ocular tissue of a patient's eye, securing the twist pick 1700 to the patient's eye. Rotation of the twist pick 1700 in the opposite direction causes the teeth 1702 to exit the ocular tissue of the patient's eye, releasing the twist pick 1700 from the patient's eye.

The twist pick 1700 also includes a head 1704 with a slot 1706. The head 1704 can, for example, engage the body 1602 of the ocular fixation device 1600. When the twist pick 1700 is secured to the ocular tissue of a patient's eye, the head 1704 can help hold the body 1602 of the ocular fixation device 1600 to the patient's eye. The slot 1706 in the head 1704 facilitates rotation of the twist pick 1700 using an instrument, such as an instrument similar to a flathead screwdriver.

The twist pick 1700 further includes an O-ring 1708. The O-ring 1708 can help to secure the twist pick 1700 into an ocular fixation device's body, such as in an opening 1612 of the body 1602. Among other things, this can help to prevent the twist pick 1700 from slipping out of the ocular fixation device's body 1602 prior to or after use.

Although FIGS. 17A and 17B illustrate one example of a twist pick 1700 used in an ocular fixation device, various changes may be made to FIGS. 17A and 17B. For example, a twist pick may not be removable from an ocular fixation device's body. Also, any other suitable twist pick design could be used to attach an ocular fixation device's body to a patient's eye.

For all of the ocular fixation devices described above, the various components or elements of the ocular fixation devices could have any suitable shapes, sizes, or dimensions. For example, various ones of the ocular fixation devices could have curved bottom surfaces, allowing the ocular fixation devices to generally lie on the surface of a patient's eye. Also, various elements or features of one of the ocular fixation devices could be used with others of the ocular fixation devices. Further, while often described as being attached to or otherwise associated with the patient's eye at the sclera, the ocular fixation devices could be attached to or otherwise associated with the patient's eye at other locations. In addition, the ocular fixation devices are often described as being used to support a surgical procedure involving the implantation of scleral prostheses into scleral tunnels in a patient's eye. However, any other suitable surgical procedure could be performed using the ocular fixation devices.

In particular embodiments, any of the ocular fixation devices described above could be sized such that the teeth, prongs, twist picks, or other fixating means for associating the ocular fixation device with an eye are secured to, contact, are coupled to, or release tissue at or near the limbus of the eye. This region of the eye may be well-suited to this type of procedure as it heals rapidly. However, each of the ocular fixation devices could have any other suitable size or shape.

The use of various mechanisms have been described above for securing or fixating ocular tissue, such as rings or other devices having teeth, prongs, pins, or twist picks. However, ocular fixation devices could use any suitable mechanism for securing or fixating ocular tissue. In this document, the phrases "means for fixating" and "fixating means" refer to any structure or portion thereof that extends from, projects from, forms a part of, or is otherwise associated with an ocular fixation device and that is pressed against, contacts, or penetrates the surface of a patient's eye. These "fixating means" include one or more teeth, prongs, pins, outcroppings, or other extensions or projections coupled to, attached to, extending from, integrated with, or otherwise associated with a ring or other structure placed proximate to the eye. The "fixating means" also include other mechanical structures such as one or more twist picks or sutures. In some embodiments, "fixating means" such as teeth may be planar or angled with respect to the structure with which the means are associated. Moreover, in this document, an ocular fixation device is said to be "associated with" an eye when the ocular fixation device is secured or attached to the eye.

It may be advantageous to set forth definitions of certain words and phrases used throughout this patent document. The terms "include" and "comprise," as well as derivatives thereof, mean inclusion without limitation. The term "or" is inclusive, meaning and/or. The term "ring" refers to a structure that is generally circular or ovoidal in shape.

While this disclosure has described certain embodiments and generally associated methods, alterations and permutations of these embodiments and methods will be apparent to those skilled in the art. For example, while shown as providing for the manual rotation or movement of one or more rings or other structures in an ocular fixation device, any suitable technology, such as a mechanical or electrical mechanism, could be used to rotate or move one or more rings or other structures in an ocular fixation device. Accordingly, the above description of example embodiments does not define or constrain this disclosure. Other changes, substitutions, and alterations are also possible without departing from the spirit and scope of this disclosure, as defined by the following claims.

What is claimed is:

1. An ocular fixation device comprising:
   a body configured to be placed over a sclera or a limbus of an eye, the body comprising multiple openings each extending through the body to a bottom surface of the body; and
   multiple twist picks configured to attach the body to the sclera or the limbus of the eye and to release the body from the sclera or the limbus of the eye, each opening of the body configured to receive one of the twist picks;
   wherein the body further comprises one or more connection points on which a surgical tool is mountable on the body after the body is attached to the eye;

wherein each twist pick comprises one or more angled projections at an end of the twist pick, each projection configured to (i) enter into the sclera or the limbus of the eye in response to rotation of the twist pick in a first direction and (ii) exit the sclera or the limbus of the eye in response to rotation of the twist pick in a second direction; and wherein each twist pick is rotatable independent of the other twist picks.

2. The ocular fixation device of claim 1, wherein the body comprises a plurality of crossbars.

3. The ocular fixation device of claim 2, wherein:
the body comprises a ring, the crossbars extending across the ring; and
the crossbars meet at a specified height above the ring.

4. The ocular fixation device of claim 1, wherein each of the one or more connection points includes an elevated area of the body adjacent to a notch in the body.

5. The ocular fixation device of claim 1, wherein the body comprises a central portion and a plurality of projections extending from the central portion.

6. The ocular fixation device of claim 5, wherein the central portion comprises an additional opening configured to enable viewing of the eye through the central portion.

7. The ocular fixation device of claim 5, wherein each projection extending from the central portion comprises one of the multiple openings configured to receive one of the multiple twist picks.

8. The ocular fixation device of claim 7, wherein the one or more connection points comprise one or more additional openings in the projections extending from the central portion.

9. The ocular fixation device of claim 1, wherein the twist picks are located inwards of an outer rim of the body.

10. The ocular fixation device of claim 1, wherein each projection of each twist pick arches circumferentially around an axis of that twist pick.

11. The ocular fixation device of claim 1, wherein the one or more angled projections comprise one or more teeth.

12. An ocular fixation device comprising:
a body configured to be placed on an eye, the body comprising multiple openings each extending through the body to a bottom surface of the body; and
multiple twist picks configured to attach the body to the eye and to release the body from the eye, each opening of the body configured to receive one of the twist picks;
wherein the body further comprises one or more connection points on which a surgical tool is mountable on the body after the body is attached to the eye;
wherein each twist pick comprises one or more angled projections at an end of the twist pick, each projection configured to (i) enter into ocular tissue of the eye in response to rotation of the twist pick in one direction and (ii) exit the ocular tissue of the eye in response to rotation of the twist pick in another direction;
wherein each twist pick is rotatable independent of the other twist picks; and
wherein the bottom surface of the body comprises a slanted edge configured to lie on a sclera of the eye.

13. A system comprising:
a surgical tool; and
an ocular fixation device comprising:
a body configured to be placed over a sclera or a limbus of an eye, the body comprising multiple openings each extending through the body to a bottom surface of the body; and
multiple twist picks configured to attach the body to the sclera or the limbus of the eye and to release the body from the sclera or the limbus of the eye, each opening of the body configured to receive one of the twist picks;
wherein the body further comprises one or more connection points on which the surgical tool is mountable on the body after the body is attached to the eye;
wherein each twist pick comprises one or more angled projections at an end of the twist pick, each projection configured to (i) enter into the sclera or the limbus of the eye in response to rotation of the twist pick in a first direction and (ii) exit the sclera or the limbus of the eye in response to rotation of the twist pick in a second direction; and
wherein each twist pick is rotatable independent of the other twist picks.

14. The system of claim 13, wherein the body comprises a plurality of crossbars.

15. The system of claim 14, wherein:
the body comprises a ring, the crossbars extending across the ring; and
the crossbars meet at a specified height above the ring.

16. The system of claim 13, wherein the body comprises a central portion and a plurality of projections extending from the central portion.

17. The system of claim 16, wherein the central portion comprises an additional opening configured to enable viewing of the eye through the central portion.

18. The system of claim 16, wherein each projection extending from the central portion comprises one of the multiple openings configured to receive one of the multiple twist picks.

19. The system of claim 13, wherein the surgical tool is configured to form a scleral tunnel in the sclera of the eye.

20. The system of claim 13, wherein the twist picks are located inwards of an outer rim of the body.

21. A system comprising:
a surgical tool; and
an ocular fixation device comprising:
a body configured to be placed on an eye, the body comprising multiple openings each extending through the body to a bottom surface of the body; and
multiple twist picks configured to attach the body to the eye and to release the body from the eye, each opening of the body configured to receive one of the twist picks;
wherein the body further comprises one or more connection points on which the surgical tool is mountable on the body after the body is attached to the eye;
wherein each twist pick comprises one or more angled projections at an end of the twist pick, each projection configured to (i) enter into ocular tissue of the eye in response to rotation of the twist pick in one direction and (ii) exit the ocular tissue of the eye in response to rotation of the twist pick in another direction;
wherein each twist pick is rotatable independent of the other twist picks; and
wherein the bottom surface of the body comprises a slanted edge configured to lie on a sclera of the eye.

22. An ocular fixation device comprising:
a body configured to be placed over a sclera or a limbus of an eye, the body comprising multiple openings each extending through the body to a bottom surface of the body, each opening configured to receive one of multiple independently-rotatable twist picks that secure the body to the sclera or the limbus of the eye and release the body from the sclera or the limbus of the eye;

wherein the openings extend through the body such that each twist pick is insertable through one of the openings in order to (i) pass one or more angled projections at an end of the twist pick into the sclera or the limbus and physically attach the one or more angled projections to the sclera or the limbus of the eye in response to rotation of the twist pick in a first direction and (ii) physically release the one or more angled projections from the sclera or the limbus of the eye in response to rotation of the twist pick in a second direction; and wherein the body further comprises one or more connection points on which a surgical tool is mountable on the body after the body is attached to the eye.

23. The ocular fixation device of claim 22, wherein the openings are located inwards of an outer rim of the body.

24. The ocular fixation device of claim 22, wherein the body further comprises a ring and a plurality of crossbars extending across the ring that meet at a specified height above the ring.

25. The ocular fixation device of claim 22, wherein:
the body further comprises a central portion and a plurality of projections extending from the central portion;
the central portion is configured to enable viewing of the eye through the central portion; and
each projection extending from the central portion comprises one of the multiple openings configured to receive one of the multiple twist picks.

26. An ocular fixation device comprising:
a body configured to be placed on an eye, the body comprising multiple openings each extending through the body to a bottom surface of the body, the bottom surface of the body configured to rest on the eye; and
multiple twist picks configured to attach the body to the eye and to release the body from the eye, each opening of the body configured to receive one of the twist picks;
wherein the body further comprises one or more connection points on which a surgical tool is mountable on the body;
wherein each twist pick includes multiple angled projections at an end of the twist pick, each projection configured to (i) enter into ocular tissue of the eye in response to rotation of the twist pick in a first direction and (ii) exit the ocular tissue of the eye in response to rotation of the twist pick in a second direction; and
wherein each twist pick is rotatable independent of the other twist picks.

* * * * *